(12) United States Patent
Castellanos

(10) Patent No.: US 7,074,183 B2
(45) Date of Patent: Jul. 11, 2006

(54) METHOD AND SYSTEM FOR IMPROVING VASCULAR SYSTEMS IN HUMANS USING BIOFEEDBACK AND NETWORK DATA COMMUNICATION

(75) Inventor: Alexander F. Castellanos, 58 Tamarack, Templeton, CA (US) 93465

(73) Assignee: Alexander F. Castellanos, Templeton, CA (US)

( * ) Notice: Subject to any disclaimer, the term of this patent is extended or adjusted under 35 U.S.C. 154(b) by 199 days.

(21) Appl. No.: 10/164,229

(22) Filed: Jun. 5, 2002

(65) Prior Publication Data

US 2002/0183599 A1 Dec. 5, 2002

Related U.S. Application Data

(60) Provisional application No. 60/295,768, filed on Jun. 5, 2001.

(51) Int. Cl.
*A61B 5/00* (2006.01)
(52) U.S. Cl. ........................ 600/300; 600/481
(58) Field of Classification Search ........ 600/300–301; 705/2
See application file for complete search history.

(56) References Cited

U.S. PATENT DOCUMENTS

| | | | |
|---|---|---|---|
| 4,601,292 A | 7/1986 | Fidel et al. | 128/660 |
| 4,745,924 A | 5/1988 | Ruff | 128/686 |
| 4,802,458 A | 2/1989 | Finsterwald et al. | 128/661.08 |
| 4,860,759 A | 8/1989 | Kahn et al. | 128/668 |
| 4,967,753 A | 11/1990 | Haase et al. | 128/662.06 |
| 5,195,519 A | 3/1993 | Angelsen | 128/660.1 |
| 5,277,187 A | 1/1994 | Pillsbury | 128/682 |
| 5,357,427 A | 10/1994 | Langen et al. | 364/413.02 |
| 5,409,009 A | 4/1995 | Olson | 128/661.08 |
| 5,409,010 A | 4/1995 | Beach et al. | 128/661.08 |
| 5,529,073 A | 6/1996 | Kielbasiewicz | 128/696 |
| 5,666,404 A | 9/1997 | Ciccotelli et al. | 379/106.02 |

(Continued)

OTHER PUBLICATIONS

Deborah F. Tate PhD, et al., "Using Internet Technology to Deliver a Behavioral Weight Loss Program," JAMA, Mar. 7, 2001, vol. 285, No. 9, p. 1172-1177.

(Continued)

*Primary Examiner*—Robert L. Nasser
(74) *Attorney, Agent, or Firm*—Hickman Palermo Truong & Becker, LLP

(57) ABSTRACT

Methods for treating vascular disease in humans and generating data representing treatment plans are disclosed. A first set of clinical vascular health data from a healthcare provider and representing a vascular health condition of a patient is received at a data center server that is communicatively coupled to a public data network. One or more vascular disease analysis algorithms are applied to the first set of vascular health data, to result in creating and storing an initial treatment plan for the patient. A second set of vascular health data is received from a monitoring device that is associated with the patient and that is communicatively coupled to the data network; the second set of data include Doppler monitor data obtained from the peripheral vascular system of the patient. One or more vascular analysis algorithms are applied to result in creating one or more supplementary treatment plans for the patient. At least one of the treatment plans includes a biofeedback interaction. The treatment plans are provided to the patient over the data network. The foregoing steps are iteratively repeated one or more times as determined by the physician and patient, resulting in improved vascular health.

22 Claims, 14 Drawing Sheets

U.S. PATENT DOCUMENTS

| | | | |
|---|---|---|---|
| 6,319,201 B1 | 11/2001 | Wilk | |
| 6,454,712 B1 | 9/2002 | Oonuki | |
| 6,612,985 B1* | 9/2003 | Eiffert et al. | 600/300 |
| 6,712,762 B1* | 3/2004 | Lichter et al. | 600/300 |
| 2002/0035316 A1* | 3/2002 | Drazen | 600/300 |
| 2002/0188182 A1* | 12/2002 | Haines et al. | 600/300 |
| 2003/0036683 A1* | 2/2003 | Kehr et al. | 600/300 |
| 2003/0208108 A1* | 11/2003 | Shewmake et al. | 600/300 |
| 2003/0212579 A1* | 11/2003 | Brown et al. | 600/300 |
| 2004/0034288 A1* | 2/2004 | Hennessy et al. | 600/300 |

OTHER PUBLICATIONS

Nancy Walsh, "Meditation Program Linked to Reduction in Carotid Intima-Media Thickness," Mar. 1, 2001, Family Practice News, p. 15.

Spacelabs Medical—Products, http://www.spacelabs.com/products/index.html, printed Jan. 17, 2000.

M. Zoler, "Framingham Score Drives Coronary Prevention," 34 eFamily Practice News (Mar. 1, 2004).

K. Rother, "Framingham Heart Study analysis reveals some primary prevention subgroups are being overlooked" (theheart.org, Oct. 2004).

A. Cohen et al., "A categorization and analysis of the criticisms of Evidence-Based Medicine," 11 Int'l J. of Medical Informatics 2 (2003).

Hartley, Carolyn P. et al., "A New Look at Disease Management," The Physician's eHealth Report, vol. 2.6 Nov./Dec. 2005, 12 pages.

Haynes, R et al., "Interventions to enhance medication adherence," Abstract, Cochrane Database Syst Rev 2005 Oct. 19; (4):CD000011.

Kaushik, R et al., "Biofeedback assisted diaphragmatic breathing and systematic relaxation versus propranolol in long term prophylaxis of migraine," Abstract, Complement Ther Med 2005 Sep.;13(3):165-74.

Krueger, KP et al., "Improving adherence and persistence: a review and assessment of interventions and description of steps toward a national adherence initiative," Abstract, J Am Pharm Assoc (Wash DC), Nov.-Dec. 2003; 43(6):668-78.

McDonald, HP et al., "Interventions to enhance patient adherence to medication prescriptions: scientific review," Abstract, JAMA Dec. 11, 2002; 288(22):2868-79.

McGinnis, RA et al., "Biofeedback-assisted relaxation in type 2 diabetes," Abstract, Diabetes Care Sep. 28, 2005;(9):2145-9.

Medicine Avenue, Inc., products description, located on the internet at <http://www.healtheheart.com>, retrieved on Jan. 3, 2004, 2 pages.

Nolan, RP et al., "Heart rate variability biofeedback as a behavioral neurocardiac intervention to enhance vagal heart rate control," Abstract, 1: Am Heart J Jun. 2005:149(6):1137.

Pittler, MH et al., "Complementary therapies for peripheral arterial disease: systematic review," Abstract, 1 Atherosclerosis Jul. 2005; 181(1):1-7, Mar. 31, 2005.

Runck, B., "What is Biofeedback?"DHHS Pub. No. (ADM) 83-1273, reprinted online by Arizona Behavioral Health Associates, P.C., date unknown, 5 pages.

Silverman, J., "Partnership Between Physician and Patient is Key to Successful Compliance," 34 eFamily Practice News 1, Jan. 1, 2004, 1 page.

Stefano, GB et al., "Integrative medical therapy: examination of meditation's therapeutic and global medicinal outcomes via nitric oxide (review)," Abstract, Int J Mol Med Oct. 2005;16(4):621-30.

Nolan, RP et al., "Heart rate variability biofeedback as a behavioral neurocardiac intervention to enhance vagal heart rate control," Abstract, 1: Am Heart J Jun 2005:149(6):1137.

Tindle, Ha et al., "Factors associated with the use of mind body therapies among United States adults with musculoskeletal pain," Abstract, Complement Ther Med Sep. 2005: 13(3):155-64.

* cited by examiner

BIOFEEDBACK--PROGRESSIVE RELAXATION TECHNIQUE

BIOFEEDBACK INTERACTION--NUTRITION

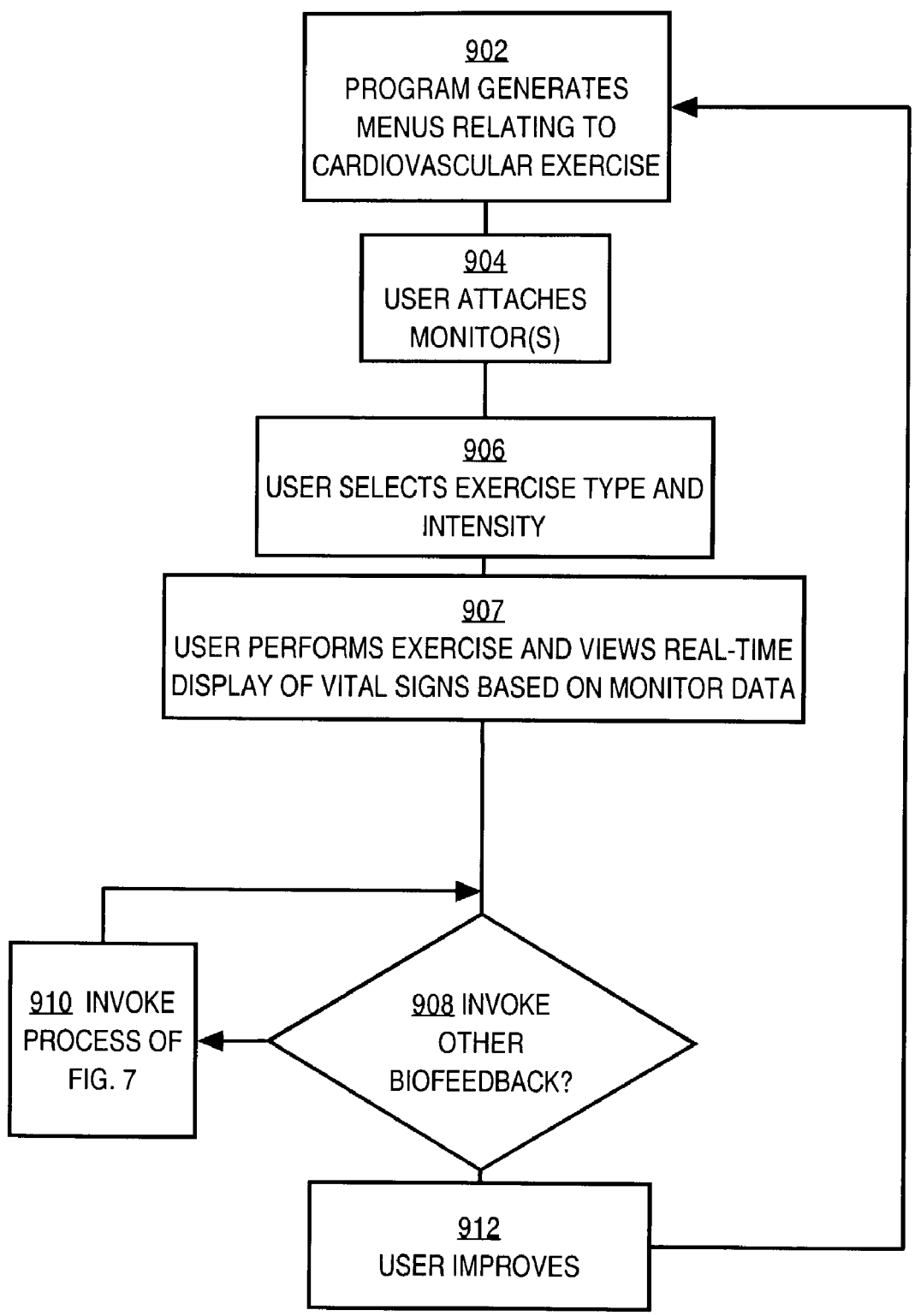

BIOFEEDBACK INTERACTION--EFFECTS OF MEDICATION

METHOD AND SYSTEM FOR IMPROVING VASCULAR SYSTEMS IN HUMANS USING BIOFEEDBACK AND NETWORK DATA COMMUNICATION

CROSS-REFERENCE TO RELATED APPLICATIONS

The present application claims domestic priority, under 35 U.S.C. §119(e), from prior provisional application number 60/295,768, filed Jun. 5, 2001, the entire contents of which are hereby incorporated by reference as if fully set forth herein.

FIELD OF THE INVENTION

The present invention generally relates to medical and physiological information processing systems. The invention relates more specifically to a method and system for improving vascular systems in humans using biofeedback and network data communication.

BACKGROUND OF THE INVENTION

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

Vascular disease occurs widely in humans and is a significant cause of premature death in many human populations. In general, vascular disease is characterized by the accumulation of fatty deposits on the walls of the arteries, causing the arterial walls to thicken and become less elastic. As a result, the flow of blood to all cells and tissues of the body is reduced. Heart disease is an example of vascular disease. Coronary artery disease is the leading cause of death in the adult population of the United States.

The medical community recognizes that the incidence of vascular disease in many populations can be reduced significantly. One way to reduce the incidence of vascular disease is to improve identification of individuals' risks for hypertension, elevated cholesterol, obesity, diabetes, smoking, inactivity and aging. Vascular disease is strongly associated with these conditions. As one commentator has observed, "[t]ools that would quantify all cardiovascular risks for use with hypertension would be a welcome and even more powerful aid than the additive technique we now have." See S. Sheps, "Treating Hypertension," Hippocrates, v. 13 no. 11 (Dec. 1999).

Presently, medical evaluation and treatment of vascular disease involves using vascular studies to determine whether an individual presenting symptoms are due to vascular disease. Such studies may involve use of procedures and machines such as magnetic resonance imaging, angiograms, thallium scans, and others, many of which are expensive to administer. As a result, they are generally used only in patients who already exhibit other symptoms of vascular disease, or who have other associated health problems. Recently the American Heart Association issued a Scientific Statement (see Circulation, 2000;101:e3 and Circulation, 2000;101 el 63) suggesting possible evaluation interventions using ankle brachial blood pressure, ultrasound and volume studies and scans. However, these methods are not widely used at the clinical level for evaluation of vascular disease.

Currently, Doppler vascular studies are performed to evaluate peripheral artery disease occurring in the arms or legs. Further, the AHA Scientific Statement identified above references prior work in using duplex vascular studies of the carotid arteries to determine and correlate anatomical changes of the coronary arteries. However, Doppler vascular studies (functional studies) of the peripheral circulatory system are not presently used to evaluate risk of cardiovascular disease, and are not used to evaluate risk in asymptomatic individuals.

Even when vascular disease is successfully identified in a patient, the current standard of care has drawbacks. For example, drugs of the class known as beta blockers are commonly prescribed, but these often cause significant complications, including depression of the heart, emotional depression, impotence, effects on diabetic control, effects on exercise, etc.

Biofeedback techniques are known for treating certain kinds of health problems by training people to respond to signals from their own bodies. See, e.g., B. Runck, "What is Biofeedback?," National Institute of Mental Health, Dept. of Health & Human Services Pub. No. (ADM) 83–1273. However, biofeedback is not presently applied to the treatment of vascular disease.

Still another problem associated with treatment of vascular disease is that health care providers lack the ability to receive and evaluate data about the then-current vascular health of an individual outside the clinical setting. Certain techniques for obtaining snapshots of data are known. For example, a Holter monitor may be used to gather an electrocardiogram from an individual during that person's normal activities away from a clinical setting. Conventional EKG electrodes are attached to the individual at a clinic, and the electrodes are coupled to a portable data collection device that measures and stores EKG data over a specified period of time, typically 24 hours. After the data collection period, the individual returns to the clinic, where the data is downloaded into a computer for analysis, and the monitor is removed. However, Holter monitors are not reliable, and may indicate cardiac disease only when it is severe. The same disadvantages are known with respect to treadmill stress tests.

Past approaches to addressing similar problems include certain online businesses. For example, "Healtheheart.com" offers online monitoring of cardiovascular diseases and online storage of clinical records, but is offered only to physicians and essentially monitors only disease conditions. "Stayhealthy.com" provides certain online tools for health evaluation, but functions only as an information service. "Wellmed.com" offers online services for personal health including personalized records and clinic files. "Lifemasters.com" provides online monitoring of patients with chronic diseases. "Dynapulse.com" provides blood pressure monitoring devices to measure cardiac function based on blood pressure readings that are uploaded over the Internet. An analysis center interprets data and provides reports. None of these approaches, however, uses biofeedback interactions, and none uses Doppler vascular data obtained from the peripheral vascular system as a global measurement tool for evaluating vascular disease.

Based on the foregoing, there is a need for a way for improved systems and methods for treatment of vascular disease.

There is also a need for a way for a healthcare provider to collect vascular data from an individual who is engaging in normal daily activities, away from a clinic, over a long period of time, such as months or years.

There is also a need for a way for a patient and a healthcare provider to concurrently have access to such vascular data.

Further, it would be beneficial to have ways for patients to engage in self-directed follow-up treatment of vascular disease through biofeedback techniques, after the initial physician evaluation.

SUMMARY OF THE INVENTION

The foregoing needs, and other needs and objects that will become apparent for the following description, are achieved in the present invention, which comprises, in one aspect, a method for improving vascular systems in humans using biofeedback and network data communication.

In one aspect, the invention provides a method for improving diagnosis, prevention, reduction and prognosis of vascular disease by evaluating the vascular system of an individual. Embodiments may involve measuring risk of vascular disease using blood pressure measurements, pulse measurements, and Doppler vascular monitoring from the peripheral vascular system, in association with biofeedback mechanisms and data communication over a network. Thus, embodiments provide methods and means for preventing, reducing, diagnosing, and determining a prognosis for vascular disease.

In other embodiments, methods for treating vascular disease in humans and generating data representing treatment plans are disclosed. A first set of clinical vascular health data from a healthcare provider and representing a vascular health condition of a patient is received at a data center server that is communicatively coupled to a public data network. One or more vascular disease analysis algorithms are applied to the first set of vascular health data, to result in creating and storing an initial treatment plan for the patient.

A second set of vascular health data is received, after initial physician evaluation, from a monitoring device that is associated with the patient and that is communicatively coupled to the data network. The second set of vascular health data include data obtained using a Doppler vascular monitor that is attached to an external location proximate to the peripheral vascular system of the patient. One or more vascular analysis algorithms are applied to result in creating one or more supplementary treatment plans for the patient. At least one of the treatment plans includes a biofeedback interaction. The treatment plans are provided to the patient over the data network. The foregoing steps are iteratively repeated one or more times as determined by the physician and patient, resulting in improved vascular health.

Embodiments are applicable to treatment of individuals who are asymptomatic or symptomatic with respect to vascular disease, hypertension, elevated cholesterol, and diabetes, and are useful in achieving stress reduction, addressing weight problems, smoking cessation, and improving personal lifestyle choices and habits.

In other aspects, the invention encompasses a computer apparatus and a computer readable medium configured to carry out the foregoing steps.

BRIEF DESCRIPTION OF THE DRAWINGS

The present invention is illustrated by way of example, and not by way of limitation, in the figures of the accompanying drawings and in which like reference numerals refer to similar elements and in which:

FIG. 9 is a flow diagram of a third biofeedback interaction that provides an exercise interaction;

DETAILED DESCRIPTION OF THE PREFERRED EMBODIMENT

A method and apparatus for improving treatment of vascular disease in humans using biofeedback and network data communication is described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments are described herein according to the following outline:

1.0 Structural and Functional Overview
2.0 Structural Details of One Embodiment
   2.1 Vascular Data Measurement Device
   2.2 Vascular Data Client Application
   2.3 Data Center Server Architecture
3.0 Functional Details of One Embodiment
   3.1 Network Biofeedback Vascular Disease Treatment Method
   3.2 Interaction with User Alone (After Initial Physician Evaluation)
   3.3 Interaction with User and Healthcare Provider
   3.4 Institutional, University and Research Uses
   3.5 Examples of Biofeedback Mechanisms
4.0 Implementation Mechanisms—Hardware Overview
5.0 Extensions and Alternatives

1.0 Structural and Functional Overview

In one aspect, the invention provides a method for improving diagnosis, prevention, reduction and prognosis of vascular disease by evaluating the vascular system of an individual. Embodiments may involve measuring risk of vascular disease using blood pressure measurements, pulse measurements, and Doppler vascular testing, in association with biofeedback mechanisms and data communication over a network. Thus, embodiments provide methods and means for preventing, reducing, diagnosing, and determining a prognosis for vascular disease.

Figure 1:
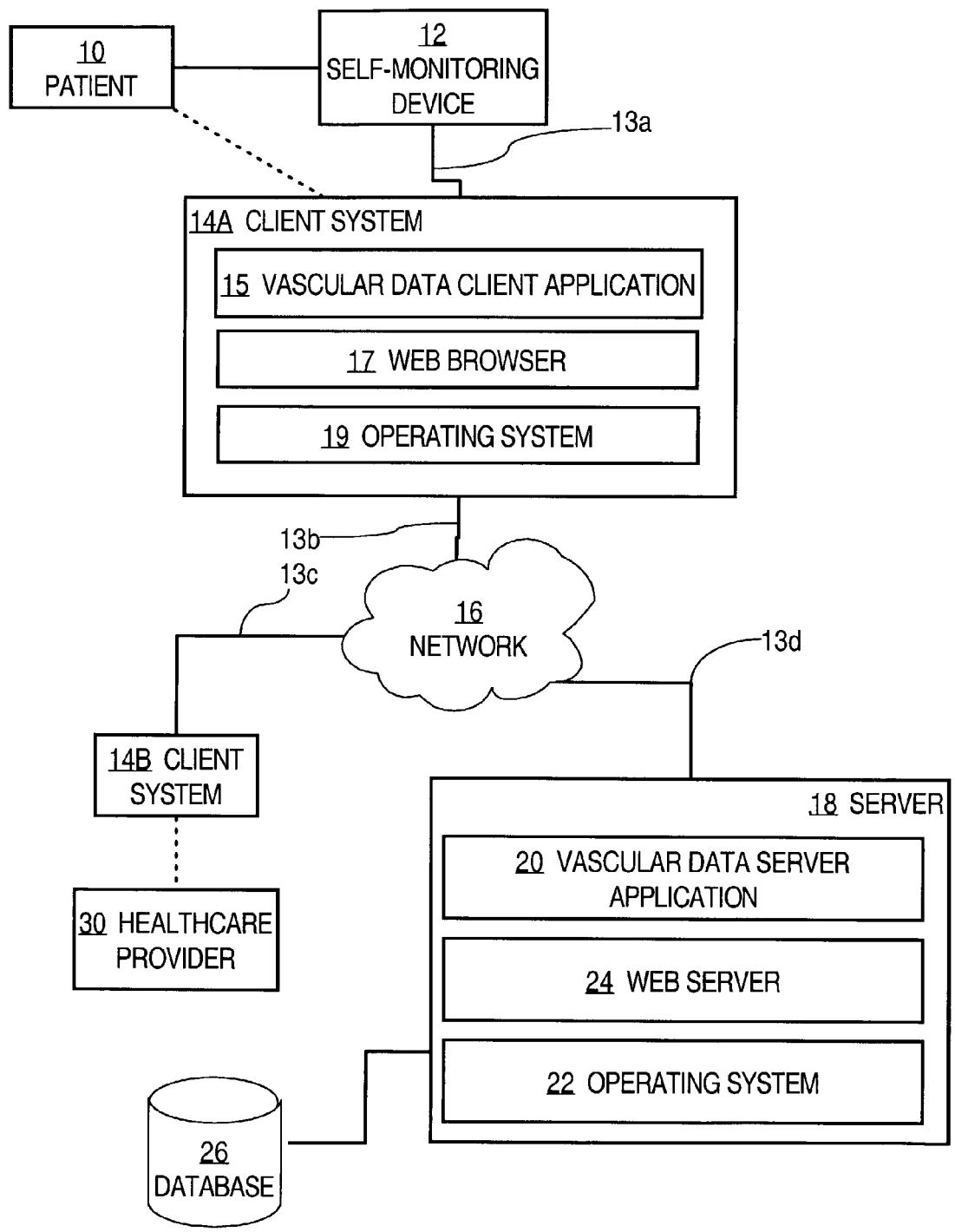
FIG. 1 is a block diagram of a system for improving vascular systems in humans, according to one embodiment.

FIG. 1 is a block diagram of a system for improving vascular systems in humans, according to one embodiment. A user or patient 10 has a monitoring device 12 that is communicatively coupled to a first client system 14A. The client system 14A may be, for example, a personal computer, personal digital assistant (PDA), wireless computing device, or workstation, etc., that is interfaced to monitoring device 12 using an appropriate hardware interface and software interface. Throughout this description, the terms "patient" and "user" are used interchangeably to refer to any individual who uses the systems and methods described herein, regardless of medical or health condition.

The monitoring device 12 is an electronic unit for monitoring and generating data relating to one or more physiological characteristics of patient 10. In one embodiment, monitoring device includes a pulse monitor, blood pressure monitor, pulse oxymeter, and vascular Doppler monitor. All such monitors may be contained within a single unit that is handheld or otherwise conveniently secured to the body. Alternatively, a plurality of separate conventional monitoring devices including a vascular Doppler monitor may be used, which are collectively represented by element 12 in the drawing figures. In still other embodiments, different monitoring devices are used; for example, monitoring device 12 may comprise a glucometer for monitoring blood glucose and diabetes using the same techniques described herein with respect to vascular disease. In one specific embodiment, monitoring device 12 comprises a vascular Doppler sensor that can gather pulse waveform data, and analysis software for generating waveforms from the sensor is provided in server 18.

Client system 14A executes a vascular data client application 15, browser 17, and operating system 19. Vascular data client application 15 provides data gathering, data communication, and treatment planning functions, and is described in further detail in a separate section below. Browser 17 is a convention HTML browser program such as Netscape Communicator, Microsoft Internet Explorer, etc. Operating system 19 may be the Microsoft Windows® operating system, Mac OS, LIKUX, or a similar system that can supervise and control higher-level applications and manage data input and output.

Client system 14A is communicatively coupled, directly or indirectly through one or more routers, switches, gateways, or other network equipment, to a public data network 16. In one embodiment, network 16 is the set of interconnected global internetworks known as the Internet.

A second client system 14B, associated with a healthcare provider 30, also is communicatively coupled to network 16. The healthcare provider 30 is a physician or other healthcare professional that is involved in treatment of patient 10. For example, healthcare provider 30 may be a personal physician of patient 10 and the client system 14B may be located in the office or clinic of that physician. The client system 14B also may be located in a location outside the clinical setting, including mobile locations or informal evaluation and treatment locations; no specific treatment location is required.

Healthcare provider 30 also represents an institution such as a hospital or other facility and its personnel who may be involved in treating patient 10. Client system 14B also executes the software elements shown with respect to client system 1 4A. In certain embodiments, client system 14A executes a physician version of client application 15, which offers functions of interest or appropriate to physicians.

In this description, the terms "physician" and "healthcare provider" are used interchangeably and are intended to broadly refer to physicians, nurse practitioners, nutritionists, chiropractors, psychologists, psychiatrists, alternative health providers, hospitals, clinics, and similar healthcare personnel or institutions.

For purposes of illustrating a clear example, in FIG. 1 only one client system 14A is shown in association with one patient 10 and only one client system 14B is shown in association with one healthcare provider 30. However, in a practical embodiment, there may be any number of client systems, patients, and healthcare providers concurrently connected to network 16, and the use of thousands or millions of such clients is contemplated.

A server 18 is communicatively coupled to network 16. A detailed description of server 18 is provided is a further section below. In one embodiment, server 18 is an enterprise-server class computer system that executes a vascular analysis application 20, Web server 24, and operating system 22. In general, server 18 provides a central point for storage of patient data, treatment plans, and user information, and for performing administrative functions such as user registration, report generation, etc. Server 18 also is communicatively coupled to a database 26 for storage of patient data, treatment plans, user information, and system support information. Database 26 may be a conventional relational database system such as Oracle 8i, Microsoft SQL Server, Microsoft Access, etc.

Network 16 is communicatively coupled to client system 14A, client system 14B, and server 18 using network links 13b, 13c, and 13d, respectively. Each link 13b, 13c, 13d to network 16 may be any kind of communication link, including wireless links or landline links.

Similarly, monitoring device 12 is coupled to client system 14A by a link 13a, which may be wireless or wired. In still another embodiment, monitoring device 12 incorporates a processor, cellular RF modem and appropriate software that enable wireless communication of data between monitoring device 12 and either server 18 or client system 14A through a network. In wireless embodiments, signals pass through one or more wireless gateways and may traverse one or more wireless networks in addition to network 16.

The server 18 and client systems 14A, 14B each are provided with means for ensuring system security and protecting the privacy of patient information. For example, hardware elements such as firewalls may be used, and software mechanisms such as passwords, user authentication, and encrypted data communications may be used.

Figure 2:
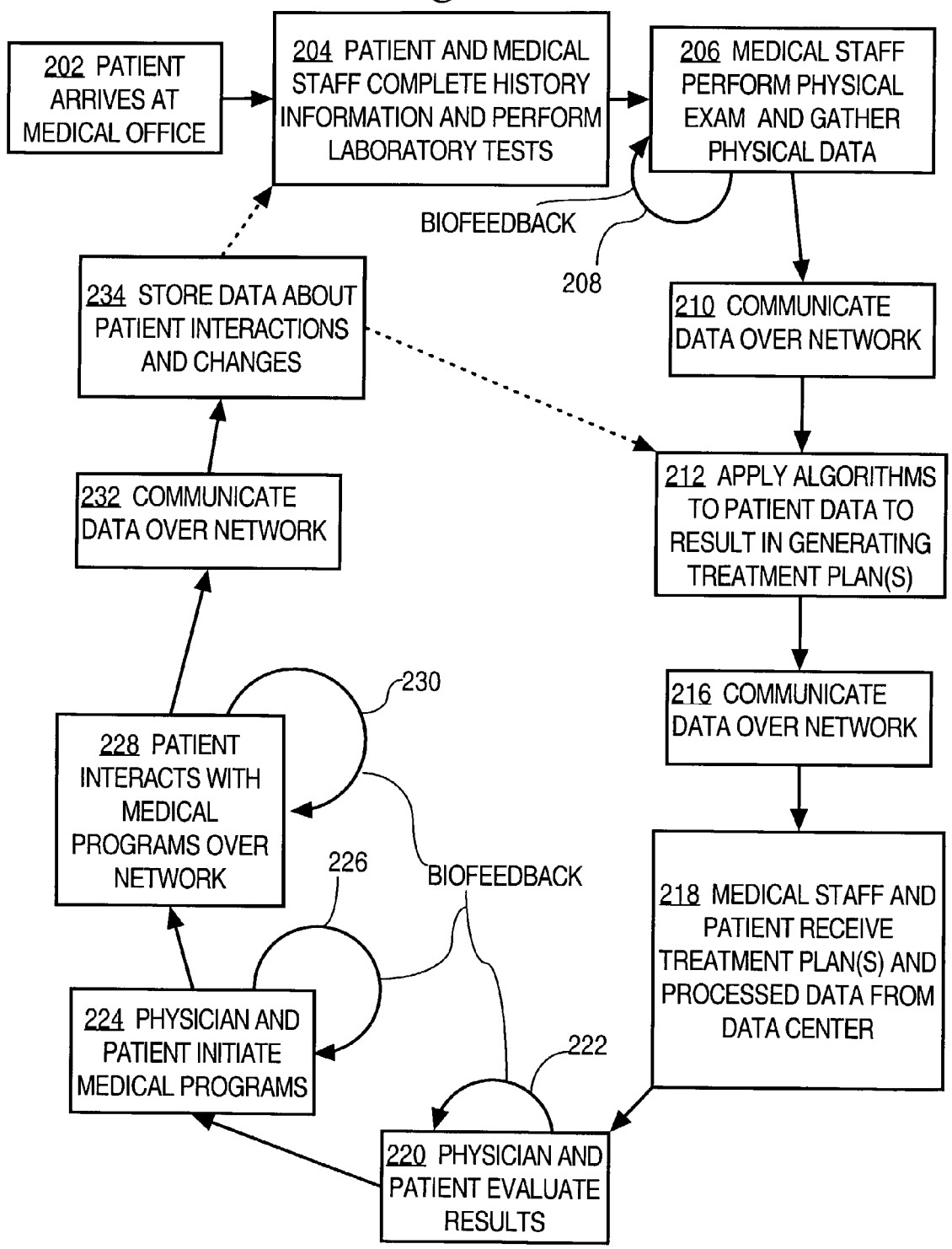
FIG. 2 is a flow diagram that provides an overview of a method of improving vascular function in humans, using the system of FIG. 1, according to one embodiment.

FIG. 2 is a flow diagram that provides an overview of a method of improving vascular function in humans, using the system of FIG. 1, according to one embodiment. In FIG. 2 and all other flow diagrams provided herein, the order of steps presented is not a required order, unless otherwise explicitly stated herein. Further, additional steps may be introduced and one or more steps may be omitted without departing from the spirit and scope of the invention.

In block 202, a patient arrives at a medical office for treatment. In alternative embodiments, described further herein, a patient may interact with elements of the system of FIG. 1 at any location; thus, interaction at a medical office is not required. In block 204, the patient provides and a healthcare provider at the medical office receives medical history information from the patient and any available pre-existing laboratory test results. For example, the patient and/or the healthcare provider complete a medical history of the patient that identifies family history factors relating to vascular disease, and evaluate any available laboratory test results.

In block 206, the medical staff receives or more physiological data measurements associated with the patient. For example, the healthcare provider performs data gathering for the patient, performs one or more physiological tests in the medical office, or requests one or more new laboratory tests. Data gathering may involve, for example, performing a physical examination of the patient and measuring one or more physiological data values of the patient, such as age, height, weight, blood pressure, body mass index, etc. Physiological testing may involve performing a Doppler vascular study, obtaining a pulse oxymetry value, determining blood cholesterol values, etc.

As indicated by arrow 208, at block 206 a first biofeedback interaction may be performed. The biofeedback interaction of arrow 208 may comprise communication between physician and patient consisting of use of 3D models, an illustration of goals, reminders of patient goals, affirmations by the patient, or other messages of the physician to the patient.

In block 210, the data obtained in block 204 and block 206 is transmitted across a public data network, such as the Internet, to a data center that has facilities for storing and analyzing the data. For example, referring again to FIG. 1, the data is sent from the client system 14B of healthcare provider 30 to server 18. Data communication between client system 14B and server 18 may use conventional techniques such as HTTP messaging, calls to Java Server Pages (JSPs), submission of data to HTML forms, etc. In one specific embodiment, data from a vascular study performed at the medical office is sent through network 16, with or without assistance by one or more wireless networks, to server 18, where a software program will analyze, interpret, and store data; the software uses one or more accepted medical algorithms and evaluates and recommends treatment programs for hypertension, elevated cholesterol, diabetes, nutrition, exercise, or stress reduction.

In block 212, the data is analyzed using one or more vascular health analysis algorithms. For example, vascular analysis application 20 (FIG. 1) is provided with the data values, executes one or more algorithms that analyze the data values, and generates one or more treatment plans and/or recommendation messages as a result.

In block 216, the treatment plans, recommendation messages, and any other data generated by the data center (e.g., server 18 of FIG. 1) are transmitted over the public data network to the healthcare provider. For example, data developed by server 18 is communicated through network 16 to client system 14B. In block 218, the medical staff and the patient receive the data that was provided by the data center. In block 220, the medical staff and the patient evaluate the data provided by the data center to determine a course of action. For example, a healthcare provider can interpret the data provided by the data center, modify the treatment plans, explain treatment plan options to the patient, etc. As part of block 220, as indicated by arrow 222, a second biofeedback event may be performed. Examples of suitable biofeedback events are described in further sections below.

In block 224, the healthcare provider and the patient initiate one or more medical programs consisting of using one or more treatments, using one or more medications, viewing videos or interacting with computer-displayed graphical 3D models. As part of block 224, as indicated by arrow 226, a third biofeedback event may be performed. In one embodiment, for example, the third biofeedback event of arrow 226 involves the patient viewing a computer display showing a graphical 3D model of the vascular system while the patient is connected to a blood pressure monitor and pulse monitor. While viewing the graphical 3D model, the patient can perform relaxation exercises or other therapy and observe, in real time, the effect of the therapy on the function of the patient's vascular system. As another example, while the patient is connected to equipment that measures and displays blood pressure and changes in Doppler vascular waveforms, the patient hears an audible signal corresponding to pulse action in the vascular system, and sees an animated graphical display of vascular wall movement that is proportional to the data that is then currently being gathered in real time.

In block 228, the patient interacts with the medical program remotely using computer access to the public data network. For example, referring to FIG. 1, while located at home, a workplace, or any other desired location, the patient connects client system 14A to network 16. The patient then interacts locally with vascular data client application 15, and remotely with server 18 and server application 20. As part of block 228, as indicated by arrow 230, a fourth biofeedback event is performed. For example, at home, the patient connects monitoring device 12 to the patient while client system 14A is connected through network 16 to server 18. The patient then performs an athletic activity, e.g., by using a home treadmill, exercise bicycle, etc. During the athletic activity, the patient may observe data values associated with the patient's vascular functions in real time on the display of client system 14A. The patient can then adjust how the patient is performing the athletic activity to favorably affect the vascular system. Alternatively, the patient can perform relaxation activities, view educational videos, etc. Use during athletic activity is not required; the monitoring device 12 may be used and data values may be observed before or after the athletic activity.

In block 232, data generated by the medical program as part of block 228 and/or block 230 is communicated over the public data network to the data center. For example, real-time vascular data, or user input to the vascular data client application 15 that was provided in non-real-time, is communicated to server 18. In block 234, the data center stores the data values representing patient interaction with the system. Block 234 may also involve modifying one or more treatment plans or recommendations that were previously generated by the data center.

Thereafter, control flows optionally to either block 204 or block 212. The steps of FIG. 2 may iterate any number of times as the patient and healthcare provider perform additional activities, biofeedback events, data gathering and analysis functions, treatment program modifications, etc.

Vascular risk evaluation performed in the foregoing manner achieves numerous useful objectives. For example, vascular disease risk may be evaluated for both asymptomatic and symptomatic patients. The clinical skills of physicians in vascular medicine are improved. Patient treatment outcomes are determined and recorded for evaluation. Patients participate in their own treatment over an extended period of time.

2.0 Structural Details of One Embodiment

2.1 Vascular Data Measurement Device

Figure 3:
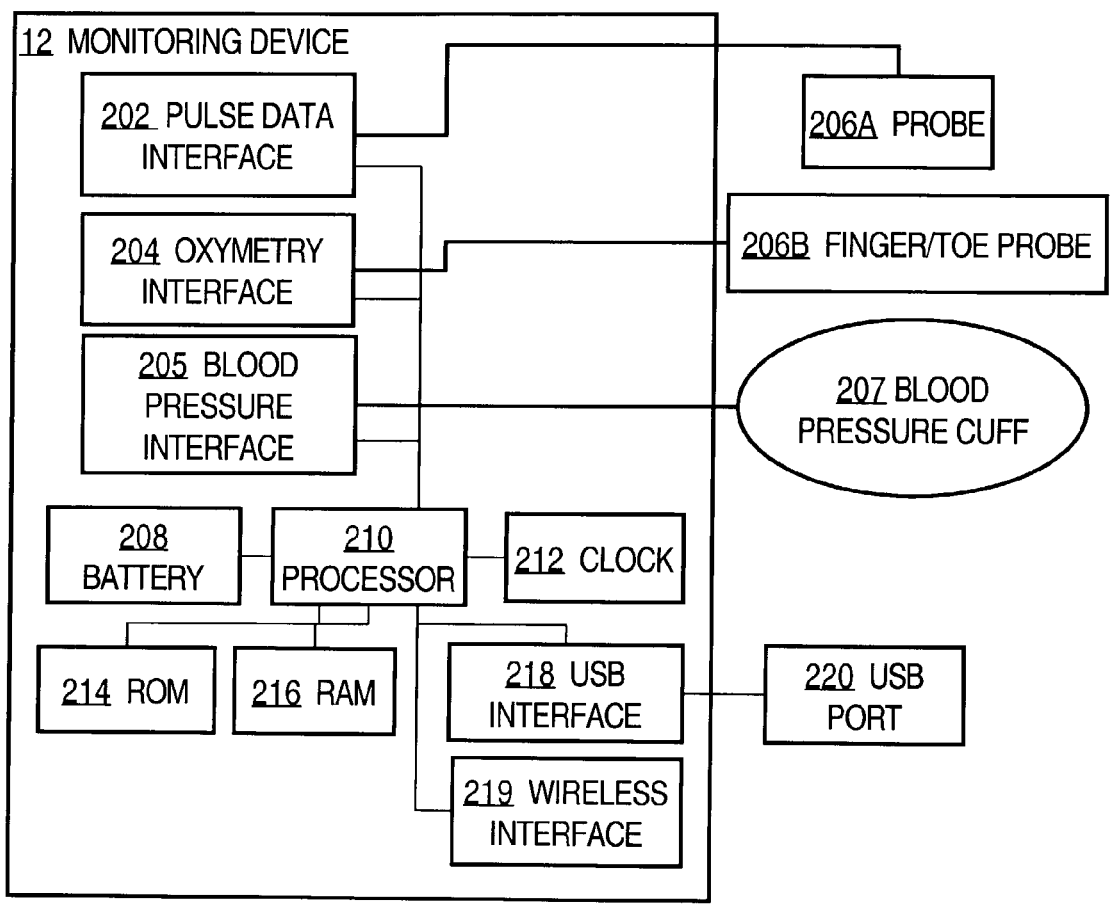
FIG. 3 is a block diagram of a vascular monitoring device, according to one embodiment.

FIG. 3 is a block diagram of a vascular monitoring device, according to one embodiment.

Monitoring device 12 comprises a processor 210 having a battery 208 that serves as a power supply and a clock 212 that provides synchronization signals. Processor 210 may be a microprocessor, micro controller, etc. Program instructions and data for controlling operation of processor 210 are stored in a read-only memory (ROM) 214 and random-access memory (RAM) 216; in certain embodiments, ROM 214 and RAM 216 are integrated with processor 210 in the form of on-chip storage. A Universal Serial Bus (USB) interface 218 terminates at a USB port 220 for connecting the monitoring device to a personal computer, peripherals, or any other suitable system.

Monitoring device 12 further comprises a pulse data interface 202, oxymetry interface 204, and blood pressure interface 205 that are respectively coupled to probes 206A, 206B and a blood pressure cuff 207. In one embodiment, probes 206A, 206B are integrated into a housing that contains and protects the other elements of FIG. 3, forming a self-contained manually graspable monitor that may be easily and conveniently used in a variety of personal physical activities. Probe 206A, for receiving pulse data, may be structured for attachment to a finger, wrist, ankle, or other external anatomical structure having a superficial pulse point. Probe 206B, for receiving oxygen saturation information, may be structured for attachment to a fingernail or toenail. Cuff 207 may be affixed to a finger, wrist, arm, ankle, etc. Further, in one specific embodiment, probe 206A functions as an acoustic vascular Doppler sensor that can gather acoustic pulse waveform data, and analysis software for generating waveforms from the sensor is provided in server 18. In this embodiment, probe 206A is secured to a pulse point at one of the extremities of the vascular system, such as the ankle. Alternatively, a separate wand, probe or other sensor may be provided for collecting acoustic Doppler vascular data, for analysis by software in server 18. Such server software is operable to create and store data representing one or more vascular data waveforms, in graphical form or in terms of raw data values, based on acoustic signals obtained by probe 206A. Thus, monitoring device 12 serves as a data gathering mechanism whereas server 18 analyzes and generates graphical images and other interpretations of the acoustic data that is gathered.

Further, in this arrangement, measurements of pulse, blood pressure, and pulse oxymetry are received by processor 210 when the monitoring device 12 is gripped by a patient or other user. Data values are determined by processor 210 in cooperation with interfaces 202, 204, 205 and provided to RAM 216 or to external systems and applications through USB interface 218. For example, under program control, client system 14A can read data values for a patient pulse, blood pressure, and oxymetry by sending appropriate messages to processor 210 through USB interface 218 and receiving responsive messages with the data values.

Optionally, monitoring device 12 incorporates an RF interface 219, antenna and appropriate software that enables wireless communication of data between monitoring device 12 and either server 18 or client system 14A through a network. With wireless communication, monitoring device 12 is easily transported by the user for use during an exercise activity, biofeedback interaction, or other activity.

2.2 Vsdvilst Data Client Application

Figure 4:
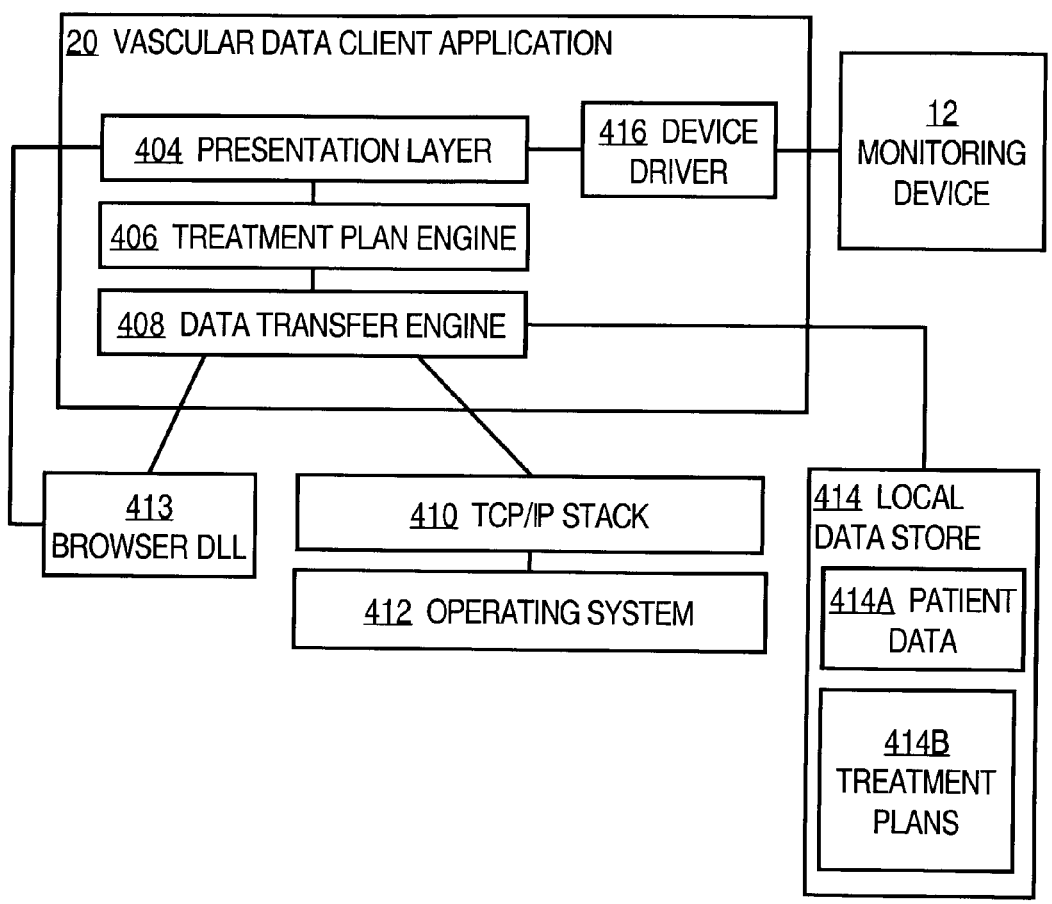
FIG. 4 is a block diagram of a vascular data and treatment application, according to one embodiment.

FIG. 4 is a block diagram of a vascular data client application, according to one embodiment.

Vascular data client application 15 principally comprises, in this embodiment, a presentation layer 404, treatment plan engine 406, and data transfer engine 408. Each of the foregoing elements may be implemented using one or more computer programs, programmatic objects, or other software elements, using any desired language system. In one embodiment, each of the foregoing elements comprises one or more Java® classes.

Presentation layer 404 is responsible for receiving data from subordinate layers and presenting the data to a user. In one embodiment, presentation layer 404 calls functions of a browser dynamic linked library (DLL) associated with an operating system 412 of the client system 14A in order to generate output that is readable using browser 17 of the client system. Alternatively, presentation layer 404 may call windowing and display functions of the operating system 412; in still another alternative, the presentation layer generates a bitmapped graphical display.

Treatment plan engine 406 is responsible for generating one or more treatment plans for a patient user, for presenting one or more treatment plans to the user, managing patient interaction with the treatment plans, and for evaluating and modifying one or more treatment plans that are received from server 18. Treatment plan engine 406 interacts with a local data store 414, which contains one or more patient data values 414A and one or more treatment plans 414B. Local data store 414 may comprise a database stored in local disk storage of client system 14A. For example, Microsoft Access may be used for local storage, or a proprietary data format may be used. Treatment plans 414B also may include one or more video streams, audio streams, graphical models of anatomic or physiological elements, etc.

Data transfer engine 408 is responsible for managing communication of data from vascular data client application 15 to other software or systems. For example, data transfer engine 408 interacts with a device interface 416 to obtain physiological data values from monitoring device 12. Alternatively, data transfer engine 408 interfaces with TCP/IP stack 410 of operating system 412 to communicate data using HTTP over a public data network.

2.3 Data Center Server Architecture

Figure 5:
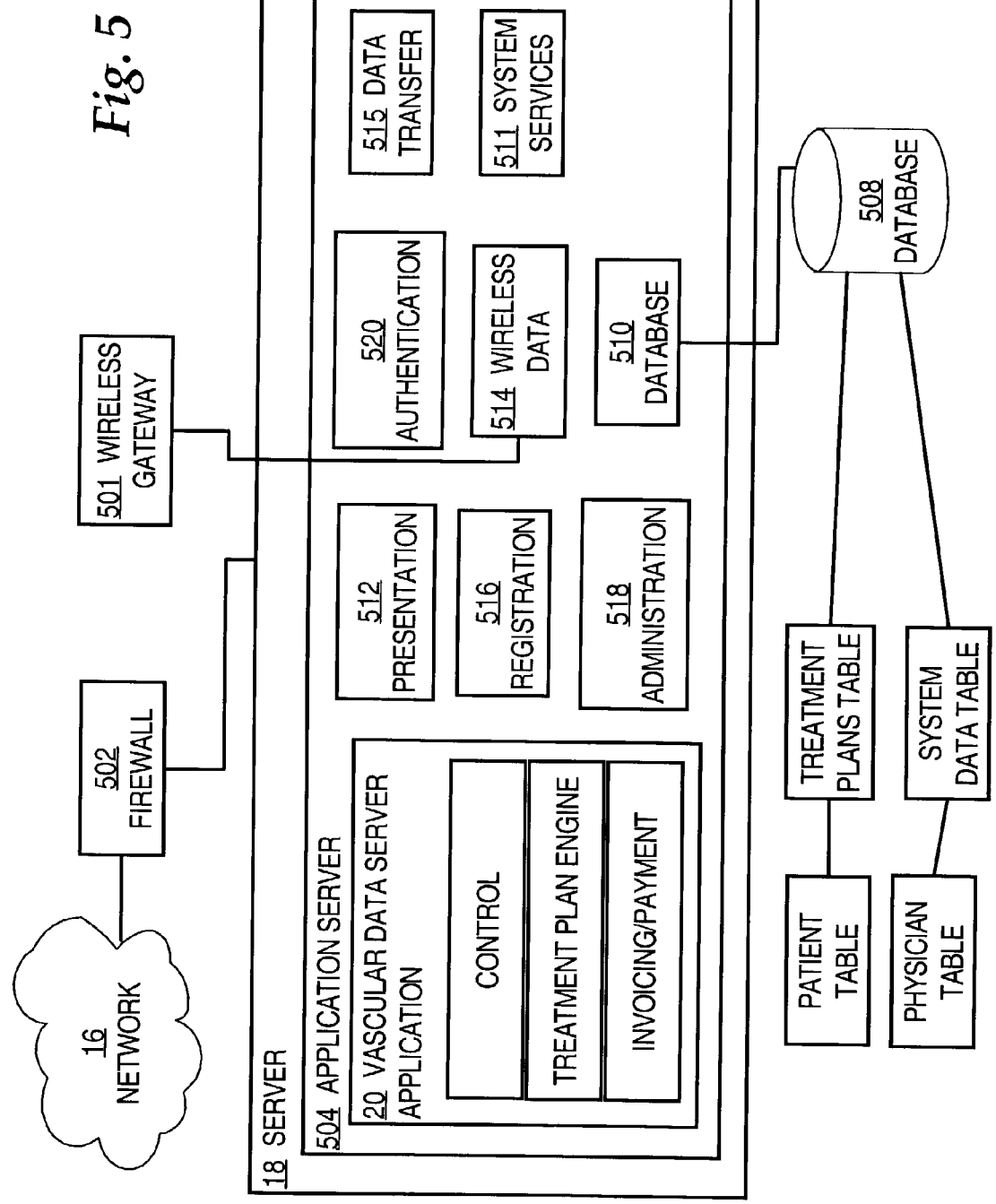
FIG. 5 is a block diagram of an architecture of a vascular data center server, according to one embodiment.

FIG. 5 is a block diagram of an architecture of a vascular data center server, according to one embodiment.

In the embodiment of FIG. 5, data center server 18 is coupled to network 16 through a firewall 502 that allows only authorized data traffic to enter the data center server. In certain embodiments, server 18 is coupled to a wireless gateway 501 that is in turn coupled to one or more wireless networks. In this arrangement, server 18 can send and receive data using traditional landline mechanisms such as the Internet or through wireless networks.

The server 18 is, in one embodiment, a server-class computer that executes an application server 504 and server application 20. An example of suitable application server software is a Java 2, Enterprise Edition (J2EE) application server such as those commercially available from WebLogic. However, embodiments are not limited to use of a J2EE application server, and any other suitable application server may be used.

Server application 20 comprises control functions, treatment plan engine functions, invoicing and payment functions, and data transfer functions. Further, in one embodiment, server application 20 interacts with a plurality of software services that perform support functions. In the embodiment of FIG. 5, such services including a presentation service 512, registration service 516, administration service 518, authentication service 520, wireless data service 514, data transfer service 515, system service 511, and database service 510.

Presentation service 512 is responsible for receiving HTTP requests from clients and rendering content. In one embodiment, content rendering is performed using a combination of Java servlets and Java Server Pages (JSPs). The presentation service 512 may comprise an image server, panel, and servlet controller. The image server is responsible for rendering images that are requested by a client browser, including images that form part of a medial program or treatment plan. The panel is responsible for receiving user interface elements of a medical program or treatment plan, and rendering them by ordering and laying out the elements. The panel also performs device-specific rendering. The servlet controller is responsible for receiving and processing servlet requests and dispatching the servlet requests to a specific subsystem. The servlet controller may comprise a plurality of different servlets, and serves as a central point for retrieving data that is used in JSP pages.

Registration service 516 is responsible for registering patient users and healthcare users in the system by recording identification information, passwords, and related data. The administration service 518 is responsible for enabling editing and configuration of the application server 504, including creation, update and deletion of users and groups of users, data communication settings, etc. Authentication service 520 is responsible for receiving requests of users to log-in to or use the system, verify passwords, and otherwise authenticate users before services are offered to them. Wireless data service 514 is responsible for dispatching data to and receiving messages from wireless data services, e.g., through wireless gateway 501.

Database service 510 manages interaction with a database 508. The database 508 may be a conventional relational database system that stores a patient data table, healthcare provider data table, treatment plan table, and system data. For security or privacy reasons, any of the foregoing tables may be maintained in a separate database server.

In one embodiment, system service 511 comprises auditing, caching, logging, offline, persistence, and time service components. The auditing component enables creation of an audit trail in database 508 that identifies functions performed by other system elements. The caching component enables caching of objects including treatment plan data, user data, images, text, and other programmatic objects. The logging component supports an operational log in database 508 for debugging and error evaluation purposes. The offline component allows a client to receive notification of changes in information that occurred when the client was disconnected from network 16; in one embodiment, the offline component interacts with an offline client plug-in at each client 14A, 14B, which is omitted for clarity. The persistence component encapsulates stored procedures that are used to read and store data. The time service component allows persistent, recurring actions to be created and scheduled.

In certain embodiments, server 18 and server application 20 provide a hosted service to one or more patients 10 and healthcare providers 30. Thus, an entity that owns or operates server 18 may function as an application service provider that makes services of server application 20 available to patients 10 and healthcare providers 30 on fee basis. Fees may be collected on a monthly or subscription basis, or on a pay-per-service basis. For example, a fee may be imposed on a healthcare provider for each clinical study that is carried out on a patient; access to resulting data may be included in the fee, or priced separately.

3.0 Functional Details of One Embodiment

The description of certain functions below may refer to actions that may be taken by a user, client or system. Alternatively, for simplicity, the description may refer only to a user; however, in that case, the term "user" is meant broadly to refer to an individual acting through an appropriate computer user interface, or to a client computer interacting programmatically with an appropriate machine interface, or to an external server, software application, or other computer system interacting programmatically with an appropriate machine interface. Thus, all references to user action are intended broadly and not as limited to individual human user action.

3.1 Network Biofeedback Vascular Disease Treatment Method

Figure 6A:
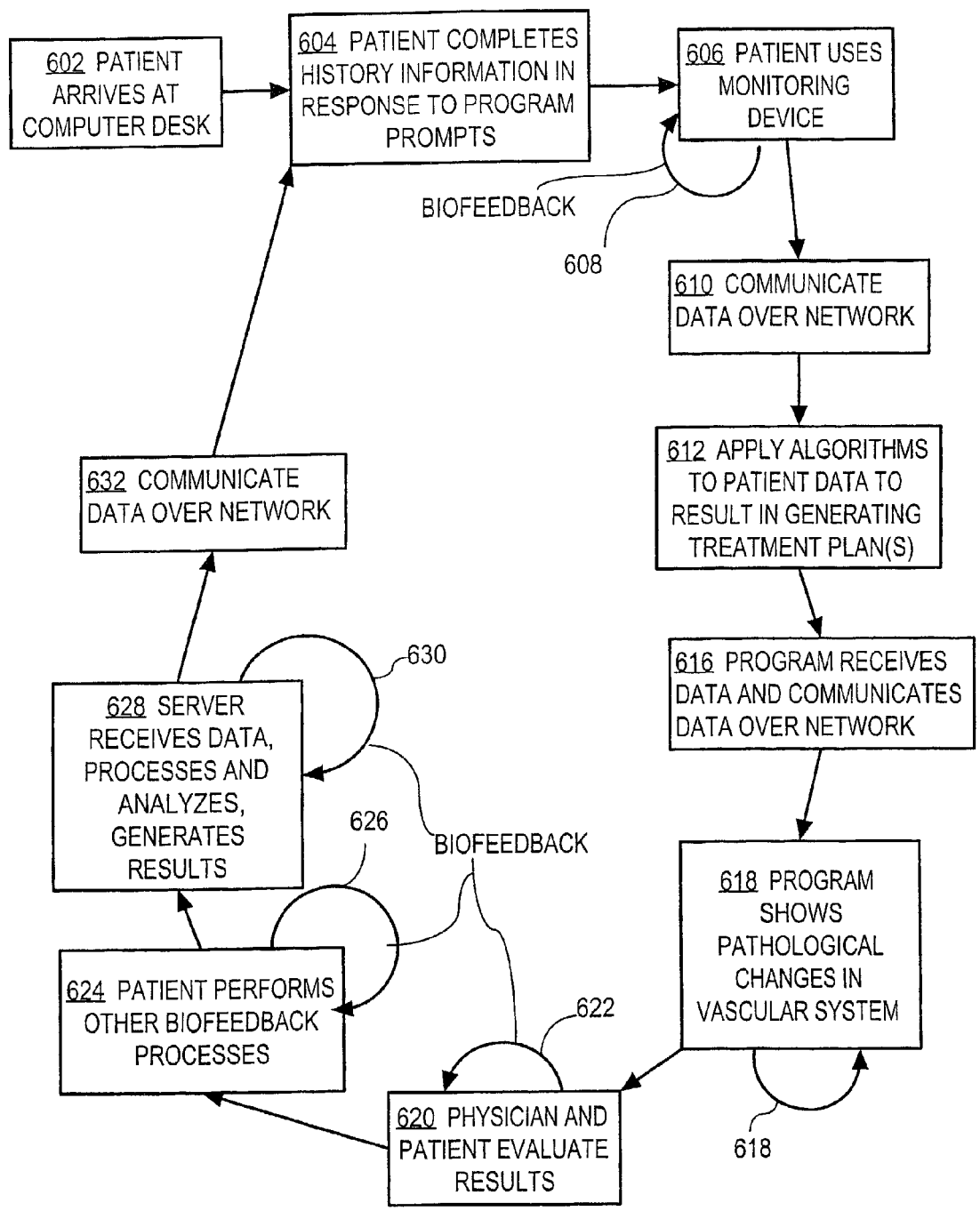
FIG. 6A is a flow diagram that illustrates one embodiment of a network biofeedback vascular disease treatment method.

FIG. 6A is a flow diagram that illustrates one embodiment of a network biofeedback vascular disease treatment method. In the approach of FIG. 6A, a patient who is undergoing treatment for vascular disease interacts with a medical program using a software program and a client system such as a personal computer. In another approach, which is described further herein, the patient may interact with a medical program that is hosted on a server that is accessed by the patient over a data network, such as the Internet. In a third approach, the patient may interact with the program under physician care in a medical office, hospital, or other healthcare site.

In another alternative embodiment, institutions such as managed care organizations, community centers, hospitals, insurance companies, and employers offering employee assistance programs may interact with the server application or client application. In still another alternative, researchers such as those affiliated with universities may interact with the server application or client application to perform research based on data stored at the server, and correlated with other investigation protocols in the area of vascular diseases evaluation, treatment, and follow up.

In each of these approaches, the medical program provides an educational component in which video information, audio information, and/or 3D graphical models show normal and abnormal physiology and structures relating to the circulatory system and heart. The patient may interact with such audiovisual information in order to understand the effect of various activities and medications on the physiology. Thus, the audiovisual interactions help to illustrate dramatic changes that can occur in vascular disease.

One or more of such audiovisual interactions may involve a biofeedback component. Thus, a patient may evaluate the patient's own circulation and other vascular characteristics by viewing and hearing the audiovisual information. For example, using a monitoring device, the client system can receive and display blood pressure and Doppler vascular waveform data for observation by the patient. The client system can concurrently audibly play acoustic data obtained from the patient using the Doppler vascular monitor in the monitoring device, enabling the patient to hear their pulse and circulatory characteristics. Over time, by applying one or more treatment plans, the patient may see and hear changes in the patient's physiology, resulting in positive improvement in vascular health.

The frequency of such interactions may vary. For example, a physician may recommend one or more periodic evaluations, such as monthly, or three times a year, depending on risk factors associated with the patient and the patient's physical condition.

Data gathered by the client system or the server may be used in long-term formal studies of populations of patients, or by the physician and patient for long-term study of the patient's improvement. For example, data gathered by the client system or the server may be used to monitor lifestyle changes, such as changes in diet, exercise, and performance of stress reduction exercises. The data gathered by the system may be used to measure the effect of medications or dietary supplements that the patient is taking. Researchers may use the data, on an aggregated or anonymous basis, to compare and correlate with other study data or other treatment approaches. For example, researchers may compare the effectiveness of biofeedback and lifestyle adjustments to invasive imaging approaches or to surgical approaches.

Further, clinical studies become more accessible in both cost and availability. Physicians and patients have permanent, continuous online access to information about patient health; physicians can remotely evaluate and monitor patients on a long-term basis without requiring an unreasonable number of clinic or office visits.

In one embodiment, the foregoing approaches may be integrated with other medical treatment. For example, the foregoing approaches may be performed in conjunction with prescription of drugs classified as calcium channel blockers, ACE inhibitors, ACE blockers, vitamin B12 or niacin therapy, etc., which have been found to avoid the side effects associated with beta-blockers, and to concurrently promote circulation in all tissues. Using these approaches, significant benefits in treatment may be realized. These benefits may include increased circulation in the extremities, heart and brain; control of migraine headache; control and reversal of early Alzheimer's disease; increased coronary circulation; increased capacity for exercise; increased circulation to the sexual organs resulting in improved sexual function; and other benefits.

The approaches described herein may include biofeedback principles, meditation, and progressive relaxation techniques in combination with physiological measurements obtained from Doppler vascular monitors and other devices. These treatment modalities are usually given and instructed by medical and paramedical providers; in contrast, the present approaches are self-administered by the patient and the physician.

The approaches herein therefore can save time and money in the course of treatment, and can increase the skills and effectiveness of the user in addressing specific physiological goals, such as to reverse or prevent cardiovascular disease and complications, for example heart attacks and strokes. The primary healthcare provider or physician can assist the user-patient with further recommendations and follow up, having seen the above exercises and treatment results.

In a similar manner, the server application and client application can assist the user to address other treatment recommendations, such as lifestyle changes. For example, embodiments can recommend one or more exercise plans. In this approach, a user attaches monitoring device 12 in order to gather data values for blood pressure, vascular pulses, and oxygen saturation, while riding a stationary bike or a treadmill at home. Client application 15 stores and analyzes the data values before the exercise regimen begins, during a period of exercise, and during the cool down period of exercise. Client application 15 is provided with safety parameters that suggest a protocol or level of exercise to the user based on the physiological data values previously gathered and stored at the server.

In another embodiment, vascular data client application 15 and vascular data server application 20 provide a nutrition evaluation and recommendation function. To support the nutrition function, the patient completes a software-driven or online questionnaire that gathers data about the type of foods recently consumed by the user, the amount of the goods, how the foods were prepared, and other data. The user submits the completed questionnaire to the server 18 using server application 20, or saves the completed questionnaire locally using client application 15. In response, applications 15, 20 provide an evaluation of the nutritional content of the foods identified by the user. The report specifies the amount of proteins, carbohydrates, fat, cholesterol, poly- and monounsaturated fats, salt, minerals and vitamins, fiber content, and other characteristics of the foods.

The nutrition function then generates one or more suggested meal plans or dietary plans. The nutrition plan function generates the dietary plans based on an evaluation of data values retrieved from database 26, such as weight, cholesterol levels, blood pressure and other factors. The nutrition plan function may also prompt the user to provide additional data values representing factors such as user preferences, etc.

In still another embodiment, input from a digital video camera or digital still camera is received at client system 14A and communicated over network 16 to server 18. Periodically during interaction with a user, client application 15 requests the user to place the camera in position for recording an image, and then receives and records one or more digital images of the user. The digital images are communicated over network 16 to server 18. Client application 15 and server application 20 may use the images for documentation of body weight; evaluation of facial expressions to measure tension and anxiety; and for recording skin torpor and coloration to assist in evaluating circulation. The digital image information also may be used to enable a healthcare provider to monitor the biofeedback functions that are performed by the user.

3.2 Interaction with user Alone (After Initial Physician Evaluation)

A specific approach involving interaction of a user or patient with client application 15 and server application 20 is now described with reference to FIG. 6A. In block 602, the patient arrives at a computer desk or similar location at which client system 14A is located. Block 602 may also involve activating a PDA or wireless device at any location; embodiments are not limited to home use.

In block 604, the patient fills out a data form to provide basic physiological information, including medical history information, in response to prompts from vascular data client application 15 (FIG. 1). Typically block 604 is performed after an initial physician evaluation of the patient. Block 604 may also involve receiving data identifying medications that the patient is then currently taking in order to facilitate risk analysis. In block 606, the user uses a monitoring device to provide blood pressure, Doppler vascular data values, and blood oxygen saturation values. Thus, block 606 may involve the user affixing monitoring device 12 to the user's body and activating a function of client application 15 that retrieves the data values from the monitoring device. The data values are stored locally at client system 14A.

As data values are gathered in block 606, a biofeedback mechanism is performed, as indicated in block 608. In one embodiment, the biofeedback mechanism of block 608 involves client application 15 generating and displaying a real-time graphical representation of the data values that the monitoring device 12 is gathering. For example, client application 15 may generate a display depicting an artery in cross-section and animate the displayed artery in coordination with data pulses that are collected by the Doppler vascular monitor. The patient can visualize the patient's physiological condition and can modify certain physical characteristics, such as breathing rate, in order to result in other internal modifications.

In block 610, data collected by the patient is sent to a data center for analysis. For example, data obtained by the monitoring device 12 and stored by client system 14A is communicated over the public data network 16 to the server 18. In block 612, one or more analysis algorithms are applied to the data provided by the patient or through the monitoring device, to result in generating one or more reports, treatment plans, or other output data that may be useful to the patient for treatment.

Block 612 may also involve performing a risk analysis for the patient, the results of which may be reported to the patient in later steps, e.g., block 616. Operation of the process of FIG. 6A may vary depending on the results of the risk analysis. For example, if the analysis of block 612 determines from the data entered by the patient that the patient is categorized as "low risk" for cardiovascular events, then the user would be able to utilize the other steps of the method in the patient's discretion. Block 612 may also involve issuing a recommendation that that patient give copies of the reports to the patient's treating physician, who may have additional recommendations.

If the user is on treatment programs with a healthcare provider, e.g., taking blood pressure medications, then block 612 may request the patient to take other action, and may prevent the patient from carrying out other steps in FIG. 6A, such as performing biofeedback interactions as described below with respect to block 624, 626, etc. Such control may be enforced by client application 15 or server application 20. For example, if the user is on blood pressure medications, is diabetic, or has other symptoms, then algorithms embodied in client application or server application 20 may instruct the patient to consult a physician for a recommendation of treatment parameters.

If the patient is categorized as "high risk," then client application 15 may recommend that the patient should not engage in certain biofeedback interactions, such as the exercise interaction described herein with respect to FIG. 9, without the direction of a personal physician. However, under control of client application 15, a patient 10 who is classified as "high risk" may still perform other functions of the program. For example, the "high risk" patient may perform biofeedback interactions relating to stress reduction, weight loss and nutritional modifications.

In block 614, the reports, treatment plans, or other result data are communicated to the patient. For example, such result data is sent from server 18 over network 16 to client system 14A for use by client application 15.

In block 616, the patient uses the received data in one or more local patient interactions. For example, client application 15 displays a graphical model that enables the patient to view pathological changes with respect to the arterial walls. As a result, a biofeedback mechanism occurs, as indicated by arrow 618.

In block 620, the patient and a physician evaluate the result data. For example, the physician can interpret the result data and provide one or more specific recommendations to the patient for improving vascular health. Alternatively, the physician can confirm the recommendations embodied in the result data and request the patient to begin a medical program as outlined in the result data. Through this process, a biofeedback interaction occurs, as indicated by arrow 622.

In block 624, the patient selects and performs one or more biofeedback processes. Specific biofeedback processes are described further herein in connection with FIG. 7, FIG. 8, FIG. 9, and FIG. 10A–10B. In one embodiment, client application 15 displays a menu of available biofeedback interactions that can be facilitated using the client application, for example, using a graphical user interface. The patient 10 provides user input to client system 14A that selects one of the biofeedback interactions. Examples include a progressive relaxation interaction, nutrition interaction, exercise interaction, an interaction relating to medication effects, etc. In response, client application 15 generates graphical displays or images, plays audio files, or plays video information to lead the patient 10 through the biofeedback interaction. As a result, biofeedback to the patient occurs, as represented by arrow 626.

Patient participation in the biofeedback interactions that are selected in block 624 may result in generating further patient physiological data or response data. In block 628, such response data is communicated to the server for processing and analysis. In response, the server analyzes and evaluates the response data based on one or more algorithms or medical calculators. Data resulting from such analysis and evaluation is presented to the patient, resulting in further biofeedback as indicated by arrow 630.

In block 632, the result data is communicated over the data network to the patient. Thereafter control may return to block 604 in which the patient may provide further physiological or history data and repeat one or more of the foregoing steps. Thus, a patient may iterate the process of FIG. 6A one or more times as determined by the patient or by the patient in consultation with a physician, to result in improvements to vascular health.

In this approach, the user can perform self-evaluation of the user's medical condition, self-treatment of one or more symptoms, and can follow up on the patient's physical progress, physiological data, and health reports.

Figure 6B:
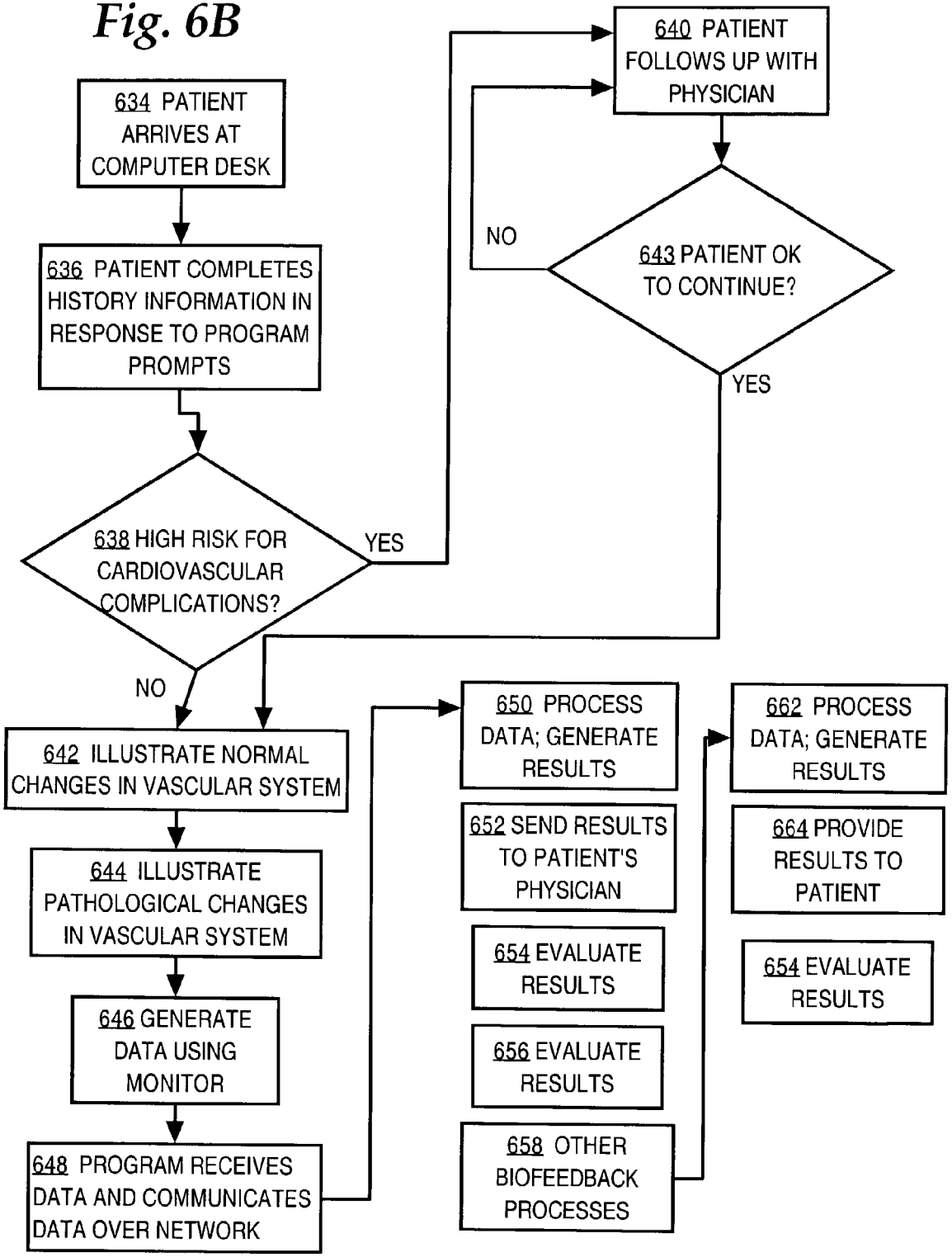
FIG. 6B is a flow diagram that illustrates a second embodiment of a network biofeedback vascular disease treatment method involving both a user or patient and a healthcare provider.
Figure 6C:
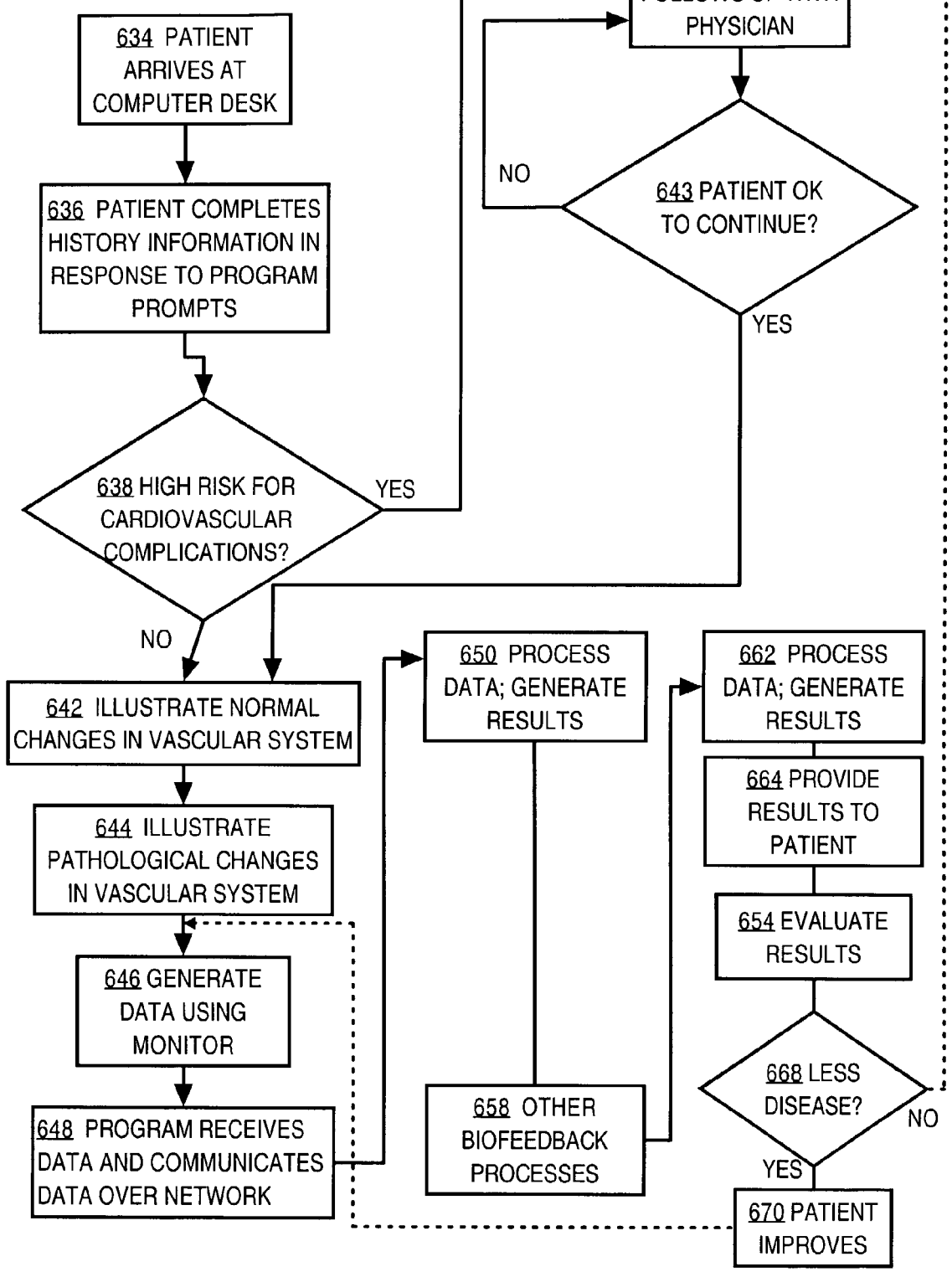
FIG. 6C is a flow diagram that illustrates a further embodiment of a network biofeedback vascular disease treatment method.

FIG. 6C is a flow diagram that illustrates a further embodiment of a network biofeedback vascular disease treatment method. In block 634, a patient arrives at a computer desk or similar facility at which a PC, PDA, or other client system is located. For example, patient 10 (FIG. 1) arrives at a location of client system 14A. In block 636, the patient provides one or more data values to the client system in response to prompts that are provided under program control. For example, client application 15 prompts the patient to enter height, weight, and similar physiological values, information identifying the patient's physician, medical history and medication information, etc. Blocks 634, 636 may involve the same processes as blocks 602, 604 of FIG. 6A.

In block 638, a test is performed to determine whether the patient should be classified as high risk. Block 638 may involve, for example, evaluating the information entered in block 636 using one or more medical calculators or algorithms that identify risk factors. Risk factors may include, for example, a high weight value indicative of morbid obesity; excessively high cholesterol values; high blood pressure values; a family history of early death because of vascular disease; dietary factors; the presence of diabetes; and other factors. If the patient is identified as "high risk" in block 638, then control is transferred to block 640 in which the client application requests the user to consult with a treating physician. After doing so, the patient may resume operation at block 634.

If the test of block 638 is negative, then control passes to block 642. In one embodiment, client application 15 generates a graphical display or audiovisual program that illustrates normal changes on the walls of arteries. Thus, an educational program that illustrates normal physiology of the cardiovascular system is provided. In block 644, client application 15 generates an additional display or audiovisual program that shows pathological changes on the walls of arteries. This provides the patient with an audiovisual educational illustration of goals of treatment and consequences of failure to address vascular disease.

The program generated as part of block 644 may follow the abnormal changes that occur with various degrees of disease of the vascular system. Video graphics may illustrate these normal and abnormal changes on the walls of the arteries. For example, an audiovisual graphical display may illustrate how the artery wall stretches normally when minimal plaque formation is present, and may illustrate how the artery is affected with increased plaque formation or arteriosclerosis. The audiovisual graphical display may also illustrate chemical components of the plaque formation, e.g., calcium, fats, cholesterol, etc.

In block 646, the user uses a monitoring device to measure physiological data values of the user. In one embodiment, monitoring device 12 is used. The monitoring device 12 may comprise a blood pressure monitor, Doppler vascular monitor, and pulse oxymeter, and may provide data values representing the patient's blood pressure, pulse, vascular acoustics and waveforms, and blood oxygen saturation to client application 15.

In block 648, the data values generated by the monitoring device are received at the client application and sent over a data network to a server at a data center. For example, HTTP communications initiated by Web browser 17 under control of client application 15 may be used to send data values in HTML forms, or other data transfer mechanisms, to server application 20 of server 18 under control of Web server 24.

In block 650, the server receives the data sent in block 648. In one embodiment, each user or patient who wishes to use the process of FIG. 6B first registers with the system of FIG. 1 and receives a username and password. The username and password are associated with a unique user account at server 18 and a segregated storage area in database 26. The data values that are sent in block 648 are stored in the user's account. Block 650 also involves processing and evaluating the physiological data values based on one or more algorithms or medical calculators. As a result, one or more sets of treatment plans, recommendations or other result data are generated.

In block 658, the patient may continue with one or more other biofeedback processes. For example, client application 15 or server application 20 may generate and present one or more menus to the patient and prompt the patient to select one or more biofeedback interactions. As examples, the biofeedback interactions of FIG. 7, FIG. 8, FIG. 9, or FIG. 10A–10B may be selected. As indicated by block 660 and the loop formed with block 658, selection and use of biofeedback interactions may iterate one or more times.

Performing the biofeedback interactions as part of block 658, block 660 may result in client application 15 generating one or more result data values. When the patient is satisfied with use of the biofeedback interactions, then control passes to block 662, in which the server processes the result data values by applying one or more algorithms or medical calculators. As a result, further result data values, treatment plans, or recommendations are generated. In block 664, the further result data values, treatment plans, or recommendations are provided to the user. In one embodiment, block 664 involves storing the further result data values, treatment plans, or recommendations in the user's account at server 18 and generating an alert message that informs the user that the further result data values, treatment plans, or recommendations are available for review or evaluation.

In block 668, a determination is made regarding whether the further result data values, treatment plans, or recommendations represent a reduction or increase in vascular health. The test of block 668 may involve self-analysis by the patient or automatic analysis by client application 15 or server application 20. If a reduction is identified, then control passes to block 640 in which a physician may perform a further clinical consultation with the patient. If an increase is identified, then improvement in health is signified, as indicated by block 670. The patient may then proceed with additional monitoring, at block 646, or with further biofeedback interactions.

3.3 Interaction with user and Healthcare Provider

FIG. 6B is a flow diagram that illustrates a second embodiment of a network biofeedback vascular disease treatment method involving both a user or patient and a healthcare provider. The approach of FIG. 6B may be used by physicians, nurse practitioners, nutritionists, chiropractors, psychologists, psychiatrists, alternative health providers, and others as an integral part of their evaluation and treatment protocol.

In one embodiment, the process of FIG. 6B is implemented using a provider-specific version of vascular data client application 15 (FIG. 1) that is executed at client system 14B in coordination with provider-specific functions of server application 20. Alternatively, client systems 14A, 14B may execute the same client application 15 in which a provider version has certain provider-specific functions enabled and a patient version has the provider-specific functions disabled.

Referring now to FIG. 6B, in block 634 a patient arrives at a computer desk or similar facility at which a PC, PDA, or other client system is located. For example, patient 10 (FIG. 1) arrives at a location of client system 14A. In block 636, the patient provides one or more data values to the client system in response to prompts that are provided under program control. For example, client application 15 prompts the patient to enter height, weight, and similar physiological values, information identifying the patient's physician, medical history and medication information, etc.

In block 638, a test is performed to determine whether the patient should be classified as high risk. Block 638 may involve, for example, evaluating the information entered in block 636 using one or more medical calculators or algorithms that identify risk factors. Risk factors may include, for example, a high weight value indicative of morbid obesity; excessively high cholesterol values; high blood pressure values; a family history of early death because of vascular disease; dietary factors; the presence of diabetes; and other factors.

If the patient is identified as "high risk" in block 638, then control is transferred to block 640 in which the client application requests the user to consult with a treating physician. After or during such a consultation, the treating physician determines whether the patient is in a condition appropriate for continued use of the process of FIG. 6B; if so, then the patient may resume operation at block 634 or block 642.

If the test of block 638 is negative, then control passes to block 642, in which client application 15 generates a graphical display or audiovisual program that illustrates normal changes on the walls of arteries or other structures of the vascular system. In block 644, client application 15 generates an additional display or audiovisual program that shows pathological changes on the walls of arteries or other structures of the vascular system. This provides the patient with an audiovisual illustration of goals of treatment and consequences of failure to address vascular disease.

In block 646, data is generated using a monitor. For example, the user uses a monitoring device to measure physiological data values of the user. In one embodiment, monitoring device 12 is used. The monitoring device 12 may comprise a blood pressure monitor, Doppler vascular monitor, and pulse oxymeter, and may provide data values representing the patient's blood pressure, pulse, vascular acoustics, and blood oxygen saturation to client application 15.

In block 648, the data values generated by the monitoring device are received at the client application and sent over a data network to a server at a data center. For example, HTTP communications initiated by Web browser 17 under control of client application 15 may be used to send data values in HTML forms, or other data transfer mechanisms, to server application 20 of server 18 under control of Web server 24.

In block 650, the server receives the data sent in block 648. In one embodiment, each user or patient who wishes to use the process of FIG. 6B first registers with the system of FIG. 1 and receives a username and password. The username and password are associated with a unique user account at server 18 and a segregated storage area in database 26. The data values that are sent in block 648 are stored in the user's account. Block 650 also involves processing and evaluating the physiological data values based on one or more algorithms or medical calculators. As a result, one or more sets of treatment plans, recommendations or other result data are generated.

In block 652, the result data are sent to the physician of the patient who was identified by the patient in block 636. In one embodiment, each physician has a user account, and block 652 involves storing a reference to the result data in an in-box at server 18 that is uniquely associated with the physician. The physician may access the in-box by using a Web browser that is executed at client system 14B to connect to server 18, logging in with the physician's username and password, accessing a portal display, and selecting the in-box. The in-box may comprise a plurality of message entries. When a message entry is selected and opened, server application 20 generates a display of pertinent patient data.

In block 654, the physician evaluates the result data. Such evaluation may involve reviewing physiological data value in comparison to a traditional patient chart, consulting references, and otherwise arriving at a determination of the patient's condition and what treatment is advisable. In block 656, the patient and the physician evaluate the result data together. Block 654 and block 656 may be combined in one operation. Block 656 may involve an office consultation with the patient in which the result data are displayed and reviewed. Alternatively, block 656 may involve the patient and physician engaging in a scheduled telephone conference or on-line chat to discuss the data. In these alternatives, both the physician and patient may concurrently access and view the result data by using Web browsers at client systems 14A, 14B, respectively, to view data in the patient account and physician account that is stored at server 18. In yet another alternative, the process of FIG. 10B is used.

In block 658, the patient may continue with one or more other biofeedback processes. For example, client application 15 or server application 20 may generate and present one or more menus to the patient and prompt the patient to select one or more biofeedback interactions. As examples, the biofeedback interactions of FIG. 7, FIG. 8, FIG. 9, or FIG. 10A–10B may be selected. As indicated by block 660 and the loop formed with block 658, selection and use of biofeedback interactions may iterate one or more times.

Performing the biofeedback interactions as part of block 658, block 660 may result in client application 15 generating one or more result data values. When the patient is satisfied with use of the biofeedback interactions, then control passes to block 662, in which the server processes the result data values by applying one or more algorithms or medical calculators. As a result, further result data values, treatment plans, or recommendations are generated. In block 664, the further result data values, treatment plans, or recommendations are provided to the user. In one embodiment, block 664 involves storing the further result data values, treatment plans, or recommendations in the user's account at server 18 and generating an alert message that informs the user that the further result data values, treatment plans, or recommendations are available for review or evaluation.

In block 666, the user's physician evaluates the further result data values, treatment plans, or recommendations that were generated. In one embodiment, block 664 may involve also sending an alert message to the physician that the user identified in block 636, so that the physician is aware that new data for evaluation is available. A physician-formatted copy of the further result data values, treatment plans, or recommendations may be stored in the physician's in-box or in association with the physician's account.

In block 668, the physician determines whether the further result data values, treatment plans, or recommendations represent a reduction or increase in vascular health. If a reduction is identified, then control passes to block 640 in which the physician may perform a further clinical consultation with the patient. If an increase is identified, then improvement in health is signified, as indicated by block 670. The patient may then proceed with additional monitoring, at block 646, or with further biofeedback interactions.

Further, in certain embodiments, a physician-specific version of client application 15 and/or server application 20 offer certain additional features and functions to physicians or other healthcare providers. For example, a physician may enroll, using software functions provided by client application 15 at client system 14B and server application 20, in a teaching program that is provided by the owner or operator of server 18 and relating to the use, interpretation, and benefits of the processes of FIG. 6A, FIG. 6B.

In another embodiment, the healthcare provider may enroll in a research organization that is involved in monitoring data gathered by server application 20 and in monitoring progress of patients who use client application 15, server application 20, and the processes described herein. In yet another embodiment, the provider may register with server 18 to join a referral list of individuals who need care or follow up, and who do not have a primary physician, or who are treated by a primary physician who does not participate in the methods described herein or in the system of FIG. 1.

In yet another embodiment, a physician may instruct server application 20 to permit other physicians or healthcare providers to access data concerning selected patients that has been gathered by the server application. In this approach, server 18 provides a centralized repository that is accessible by other physicians who are researching or treating vascular disease.

A healthcare provider may use the methods described herein only for an initial evaluation of a patient. The provider may choose to follow one or more different treatment methods depending on his specialty and patient factors. The provider may participate in the system and methods described herein only with respect to blood pressure and vascular health, or with respect to all other physiological functions described herein.

3.4 Institutional, University and Research uses

The system and methods described herein also may be used by institutions to facilitate various healthcare programs. For example, client application 15 and server application 20 may be used, specifically as described herein or with appropriate modifications, in weight reduction programs, stress reduction programs, cancer treatment programs and support groups, diabetes treatment programs, cardiac rehabilitation programs, etc. In this approach, participants in such programs interact with one or more client systems 14A under control of client application 15, in the same manner described above. Administrators, supervisors, or physicians in charge of the institutional programs may access data and participate in the system using client systems 14B and access to patient data in server 18 under control of server application 20.

In the university and research context, the system and methods described herein may be used for evaluation of patients with potential vascular disease in addition to those recommendations made in the American Heart Association Scientific Statement referenced above. The system and methods described herein can be used in conjunction with other currently used and on-going monitoring evaluations, such as coronary and cardiac catheterizations, ultrasound evaluations of cardiac status, etc.

3.5 Biofeedback Mechanisms

In any of the foregoing embodiments, the user can interact further by selecting one or more biofeedback options or exercises. For example, assume that a patient is viewing an educational display generated by the program. The program prompts the user to select a biofeedback exercise. The patient selects a "Beach Stroll" biofeedback exercise. In response, the client system displays an oceanfront scene on the display of the client system. The client system then plays, using a sound system integrated into the client system, an audio file that states the following:

"Imagine yourself walking on the beach. You are concentrating on the sounds of the waves. You are breathing slowly. You feel the cool misty ocean air. You are feeling the sand on your feet, on your hands, you are sitting. You are aware of the sun shining on you, then you are feeling warm and you are feeling this warmth passing to the various regions of your body. The warmth starts at your face, then this travels to your arms and all the way down to your fingertips. These sensations travel to the back muscles and the shoulders. These sensations go to the chest and your belly muscles and you are aware of these muscles moving in and out with each slow breath. These sensations continue down to your legs, the warm feeling continues to travel down to your feet and you are more aware of the sand ,the water, and the warmth of the sun."

This example is merely one of several options offered to a user by the client application. The biofeedback mechanisms may be used daily, weekly, or according to any other schedule determined by the patient or physician. These sessions improve stress reduction and management, and assist in treatment and reversal of arteriosclerosis.

Figure 7:
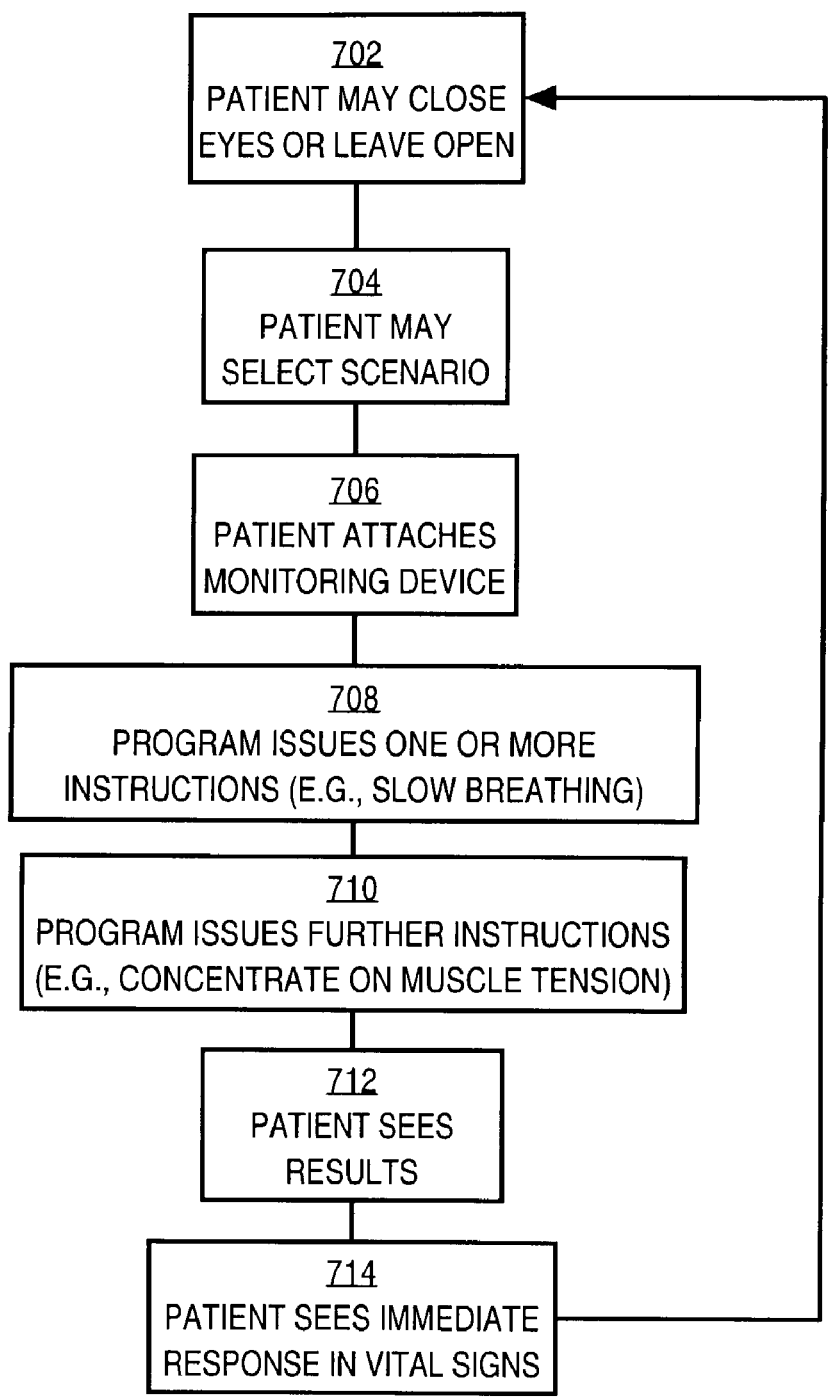
FIG. 7 is a flow diagram of a first biofeedback interaction that provides a progressive relaxation technique.

FIG. 7 is a flow diagram of a first biofeedback interaction that provides a progressive relaxation technique. Steps of FIG. 7 may be implemented using software instructions as part of client application 15.

In block 702, client application 15 instructs the patient regarding viewing the display screen as the interaction occurs in subsequent steps. For example, client application 15 causes client system 14A to play an audio file that states, "you may close your eyes or leave them open, whichever you prefer." In block 704, the patient is prompted to select a relaxation scenario such as walking on the beach, walking in the forest, etc. The scenarios are selected to assist the patient in achieving relaxation.

In block 706, the user attaches a monitoring device. For example, the user attaches a monitoring device that provides a blood pressure monitoring capability, Doppler vascular monitor, and pulse oxymeter. Alternatively, separate monitoring devices that perform similar functions may be attached.

In block 708, one or more instructions are issued to the user. For example, client application 15 instructs the user to adopt slow breathing, and to concentrate on air movement through the respiratory tract. In block 710, one or more further instructions are issued. For example, client application 15 instructs the user to concentrate on allowing muscle tightness around the neck shoulders to loosen, and optionally may issue one or more further instructions. Concurrently, client application 15 displays graphical images and video information, and plays sound files that represent the selected scenario. Thus, the audible instructions and video display are coordinated to present a visual and auditory experience corresponding to the selected scenario, in a way that induces relaxation.

Also concurrently, result data and other data representing vital signs of the user are displayed, as indicated in block 712 and block 714. For example, vital sign data is displayed in real time on the video display of client system 14A. In this context, vital signs include blood pressure, pulse, oxygen content, and vascular waveforms. Thus, the user is able to see, in real time, responses and changes in the vital signs, and correlate the changes with the patient's level of relaxation.

The user also can use the process of FIG. 7 to induce a reverse effect for purposes of evaluation and observation. For example, in response to appropriate instructions by client application 15, the user may see how blood pressure, pulse, oxygen content, and vascular waveforms are altered during stressful conditions or thought processes.

Figure 8:
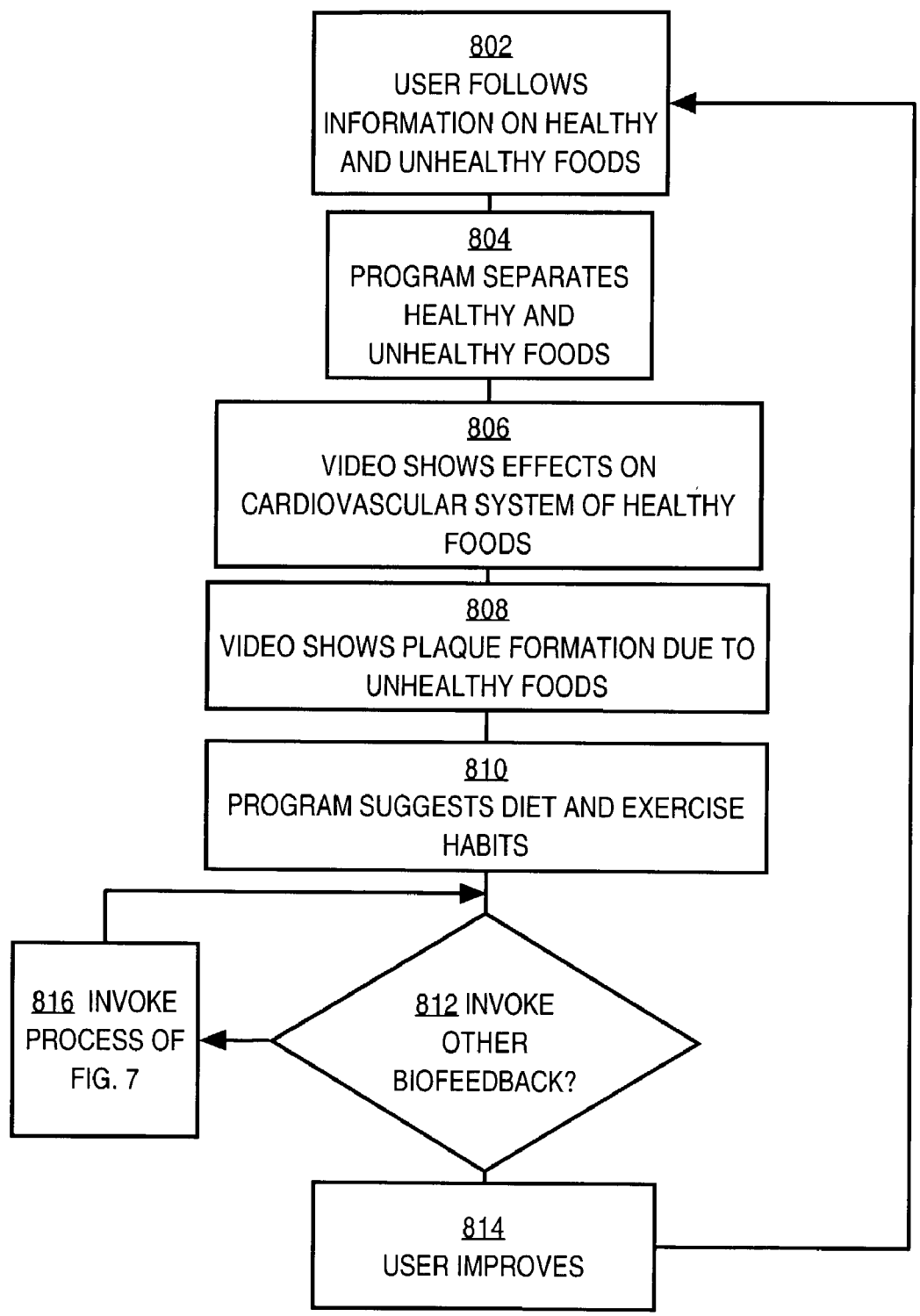
FIG. 8 is a flow diagram of a second biofeedback interaction that provides a nutrition interaction.

FIG. 8 is a flow diagram of a second biofeedback interaction that provides a nutrition interaction.

In block 802, client application 15 causes client system 14A to display one or more audiovisual programs relating to benefits of good nutrition. For example, client application 15 may generate a display of information that separates healthy foods in comparison to unhealthy foods, as shown by block 804. As indicated in block 806, audiovisual programs about healthy foods may be coupled by video illustrations on the effects of the cardiovascular system in their reversal and treatment of arteriosclerosis. Similarly, as shown by block 808, audiovisual programs about unhealthy foods may be presented in association with audiovisual information about accelerated formation of plaque formation on the artery wall. In block 810, client application 15 may provide visualization exercises for the user to follow on how healthy foods benefit better health and fitness.

In block 812, the user is prompted to select whether to perform another biofeedback interaction, such as the progressive relaxation biofeedback interaction of FIG. 7. If the user selects such an interaction, it is invoked or performed, as shown by block 816. In either case, improvement in user health occurs, as indicated by block 814.

FIG. 9 is a flow diagram of a third biofeedback interaction that provides an exercise interaction.

In one embodiment, the process of FIG. 9 provides a biofeedback interaction in the area of cardiovascular aerobic exercise, as shown by block 902. In general, a user follows illustrations generated by client application 15 on the effects of aerobic exercise on the cardiovascular system, and which show the benefits of aerobic exercise. In block 904, the user attaches a monitoring device, or one or more separate monitoring devices, as in block 706 of FIG. 7.

In block 906, client application 15 prompts the user to select an exercise type and complexity. The user then participates in the selected or recommended exercises using equipment available to the user, and with the monitoring device attached to the user. For example, in one embodiment, the user may choose from among walking in place, performing hand grips, performing knee bends, performing modified squats, performing arm exercises, etc. Concurrently, data representing vital signs of the user are displayed in real time on the video display of client system 14A. In this context, vital signs include blood pressure, pulse, oxygen content, and vascular waveforms. Thus, the user is able to see, in real time, responses and changes in the vital signs, and correlate the changes with the patient's level of exercise.

In block 908, the user is prompted to select whether to perform another biofeedback interaction, such as the progressive relaxation biofeedback interaction of FIG. 7. If the user selects such an interaction, it is invoked or performed, as shown by block 910. In either case, improvement in user health occurs, as indicated by block 912.

Figure 10A:
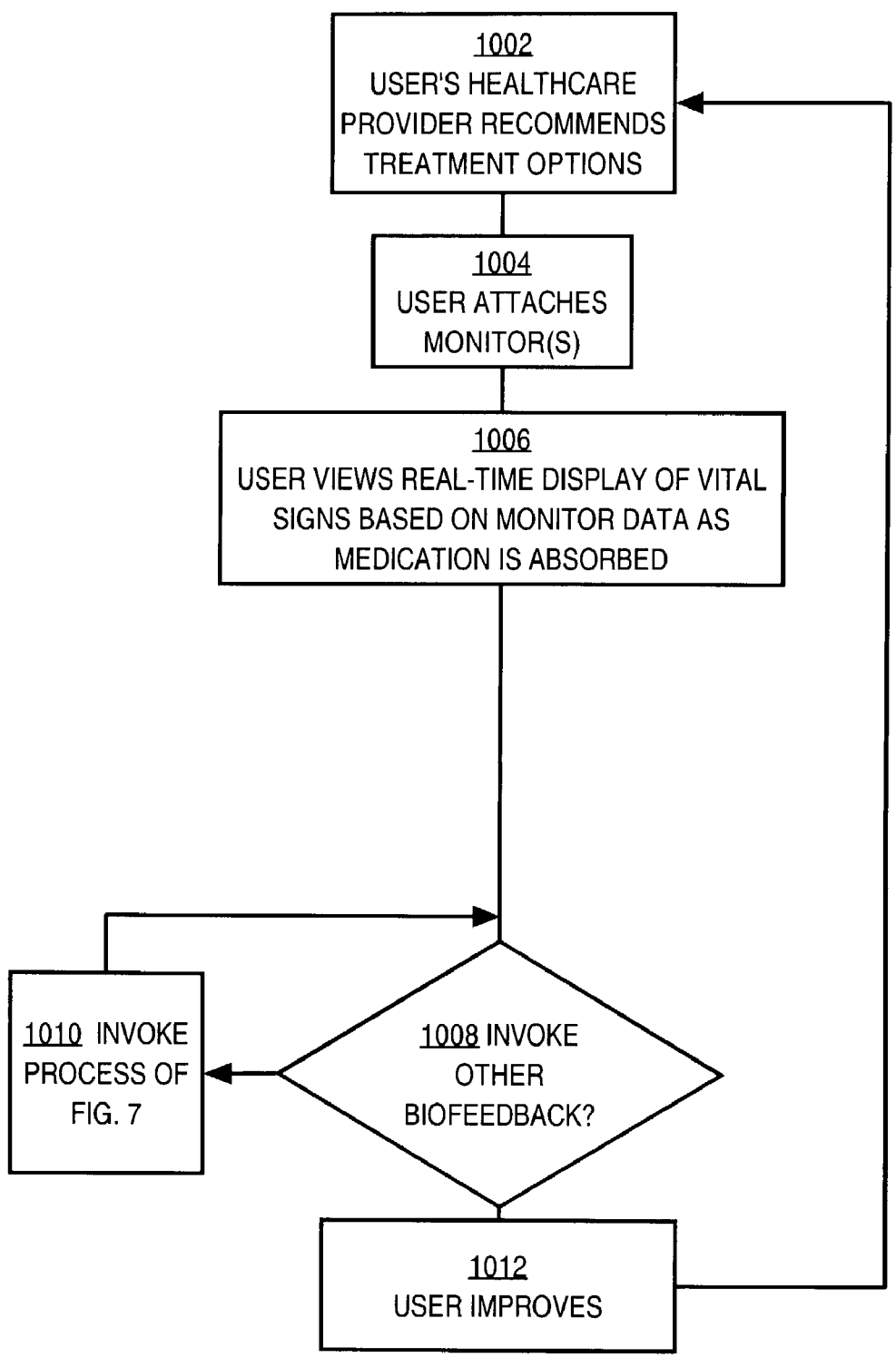
FIG. 10A is a flow diagram of a fourth biofeedback interaction that addresses effects of cardiovascular medications.
Figure 10B:
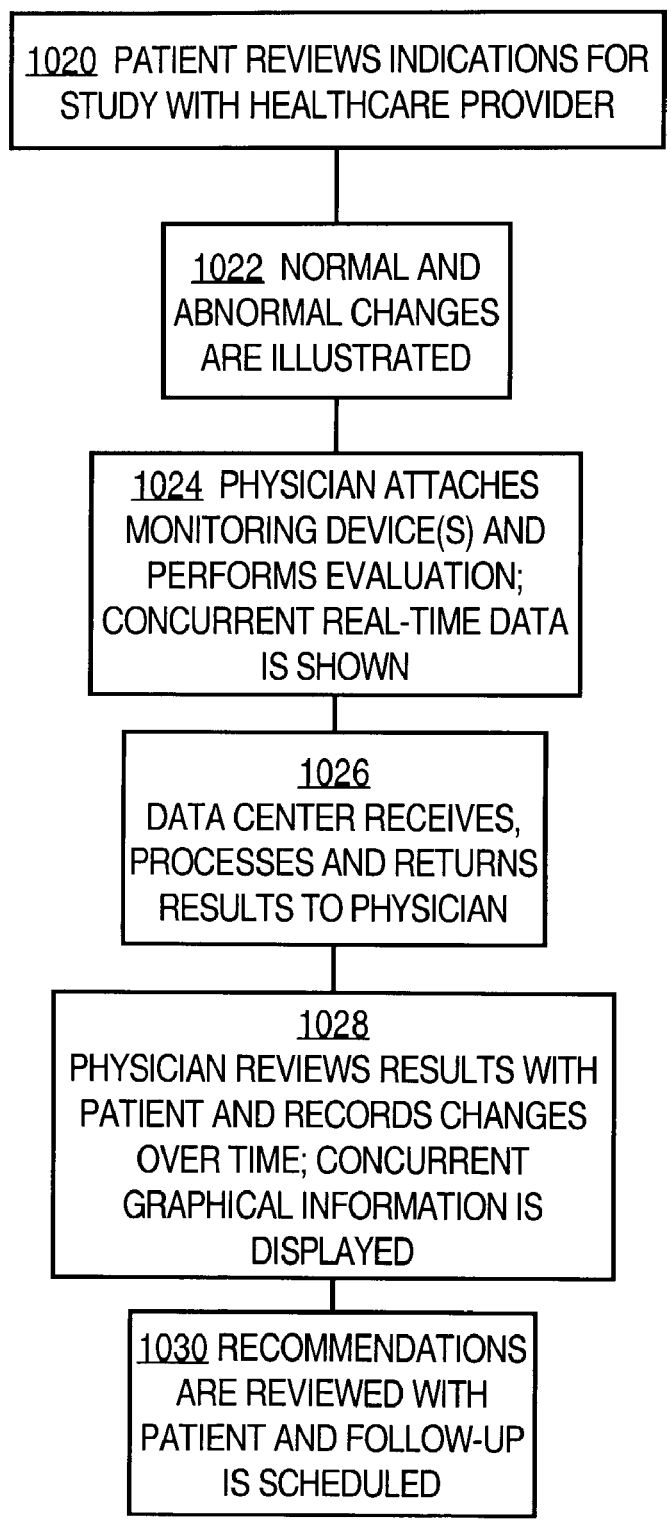
FIG. 10B is a flow diagram of a fifth biofeedback interaction that relates to physician review of data results.

FIG. 10A is a flow diagram of a fourth biofeedback interaction that addresses effects of cardiovascular medications. In general, the biofeedback interaction of FIG. 10A may be used to monitor the effects of cardiovascular medications that may have been prescribed by a physician, as indicated by block 1002. Block 1002 also may involve using technical means to integrate the user's physician into the biofeedback interaction so that the physician can monitor changes in the user's physiology. For example, block 1002 may involve the user and physician concurrently using separate instances of client application 15, at client system 14A, 14B, respectively, to view real-time patient physiological data as cardiovascular medications are absorbed by the patient. Alternatively, the process of FIG. 10A may be performed in a clinical setting, enabling direct physician monitoring.

In block 1004, the user attaches a monitoring device, or one or more separate monitoring devices, as in block 706 of FIG. 7. Block 1004 may also involve administering one or more medications to the patient and waiting for an appropriate time to enable the patient to begin to absorb the medications.

Concurrently, data generated by the monitoring device and representing vital signs of the user are displayed in real time on the video display of client system 14A. In this context, vital signs include blood pressure, pulse, oxygen content, and vascular waveforms. Thus, the user is able to see, in real time, responses and changes in the vital signs as medication is taken, and correlate the changes with the patient's level of medication.

In block 1008, the user is prompted to select whether to perform another biofeedback interaction, such as the progressive relaxation biofeedback interaction of FIG. 7. If the user selects such an interaction, it is invoked or performed, as shown by block 1010. This enables the user to see the benefits of stress reduction in combination with medication interactions. In either case, improvement in user health occurs, as indicated by block 1012.

In still another biofeedback interaction, the user may compare data obtained at one point in treatment with similar data obtained at another point. This interaction enables the patient to perform a comparison, over a long-term follow-up period, of changes in the patient's vascular health. In particular, a user or physician may use such a biofeedback interaction to monitor the long-term beneficial changes that occurs with behavioral modifications. Client application 15 measures waveform data obtained from the Doppler vascular monitor as part of monitoring device 12 to determine elasticity of the artery, which may be correlated with the amount of plaque formation on the artery wall. The user may perform periodic comparisons of such parameters in order to follow changes in vascular health.

FIG. 10B is a flow diagram of a fifth biofeedback interaction that relates to physician review of data results. In block 1020, a patient reviews one or more indications for study with a physician. For example, prior clinical tests, laboratory results, history information, or other factors may identify indications such as hypertension or high cholesterol that need study. In block 1022, normal and abnormal changes are illustrated. Block 1022 may involve using a physician-specific version of client application 15 to display one or more audiovisual programs or graphical models of vascular anatomy and function.

In block 1024, the physician attaches one or more physiological monitoring devices and performs an evaluation of the patient. Concurrently, real-time data gathered from the monitoring devices is displayed by client application 15 using client system 14B. The data is uploaded, simultaneously or subsequently, to a data center that stores the data in association with a physician account or patient account for later analysis. As shown in block 1026, the data center receives, processes and returns result data to the physician.

In block 1028, the physician reviews the result data with the patient and records one or more changes in the patient's health that have occurred over time. Such recordation may occur in a traditional patient chart or using client application 15 to enter appropriate values. Concurrently, one or more graphs or audiovisual programs relating to changes in the patient's health are displayed. In this manner, the patient experiences biofeedback by visually seeing or audibly experiencing positive or negative changes in health. In block 1030, one or more recommendations of client application 15 or of the physician are reviewed with the patient, and further follow-up may be scheduled.

4.0 Implementation Mechanisms—Hardware Overview

Figure 11:
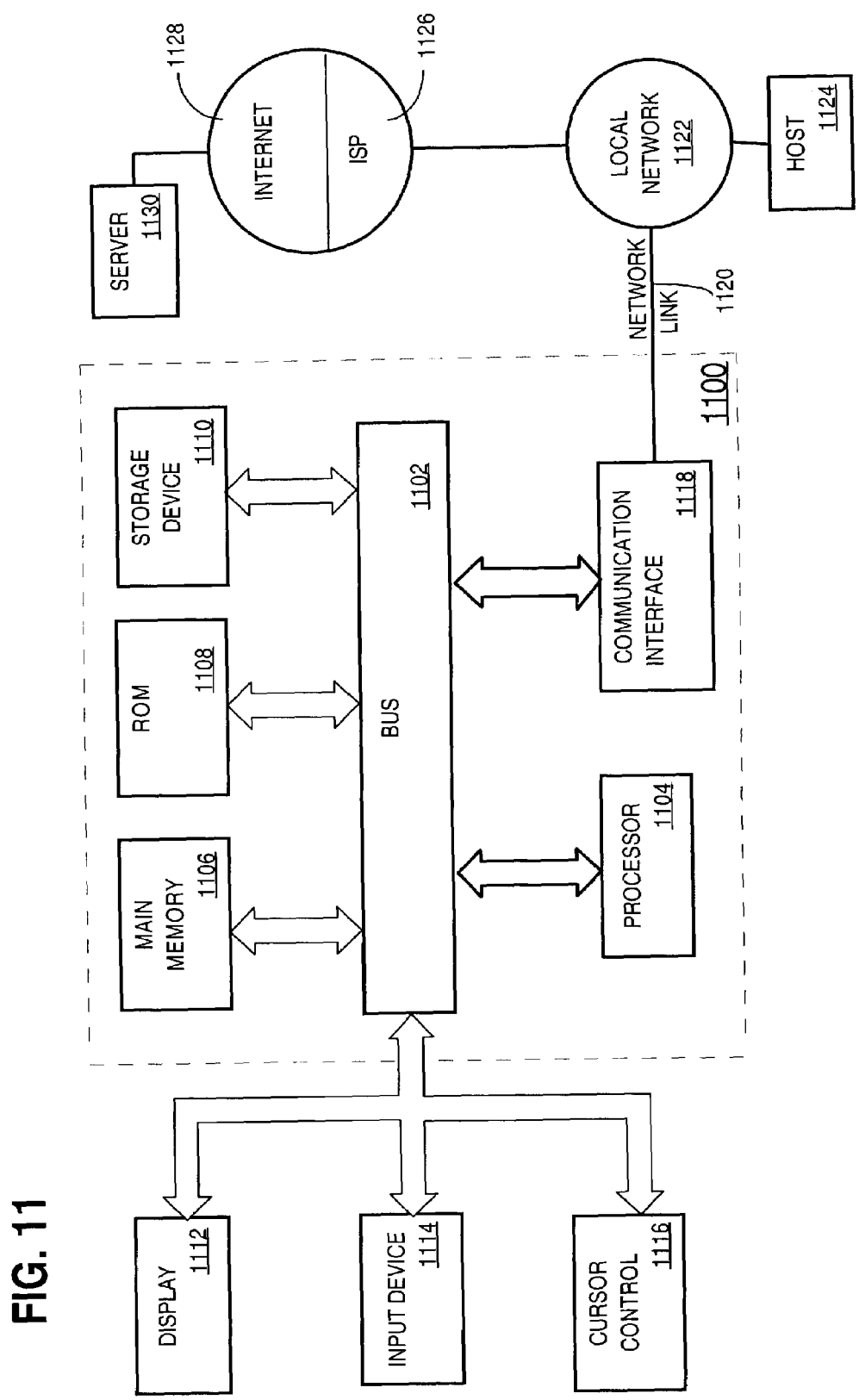
FIG. 11 is a block diagram that illustrates a computer system upon which an embodiment may be implemented.

FIG. 11 is a block diagram that illustrates a computer system 1100 upon which an embodiment of the invention may be implemented. Computer system 1100 includes a bus 1102 or other communication mechanism for communicating information, and a processor 1104 coupled with bus 1102 for processing information. Computer system 1100 also includes a main memory 1106, such as a random access memory ("RAM") or other dynamic storage device, coupled to bus 1102 for storing information and instructions to be executed by processor 1104. Main memory 1106 also may be used for storing temporary variables or other intermediate information during execution of instructions to be executed by processor 1104. Computer system 1100 further includes a read only memory ("ROM") 1108 or other static storage device coupled to bus 1102 for storing static information and instructions for processor 1104. A storage device 1110, such as a magnetic disk or optical disk, is provided and coupled to bus 1102 for storing information and instructions.

Computer system 1100 may be coupled via bus 1102 to a display 1112, such as a cathode ray tube ("CRT"), for displaying information to a computer user. An input device 1114, including alphanumeric and other keys, is coupled to bus 1102 for communicating information and command selections to processor 1104. Another type of user input device is cursor control 1116, such as a mouse, trackball, stylus, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane.

The invention is related to the use of computer system 1100 for digitally signing shared dynamic content. According to one embodiment of the invention, digitally signing shared dynamic content is provided by computer system 1100 in response to processor 1104 executing one or more sequences of one or more instructions contained in main memory 1106. Such instructions may be read into main memory 1106 from another computer-readable medium, such as storage device 1110. Execution of the sequences of instructions contained in main memory 1106 causes processor 1104 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1104 for execution. Such a medium may take many forms, including but not limited to, non-volatile media, volatile media, and transmission media. Non-volatile media includes, for example, optical or magnetic disks, such as storage device 1110. Volatile media includes dynamic memory, such as main memory 1106. Transmission media includes coaxial cables, copper wire and fiber optics, including the wires that comprise bus 1102. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1104 for execution. For example, the instructions may initially be carried on a magnetic disk of a remote computer. The remote computer can load the instructions into its dynamic memory and send the instructions over a telephone line using a modem. A modem local to computer system 1100 can receive the data on the telephone line and use an infrared transmitter to convert the data to an infrared signal. An infrared detector can receive the data carried in the infrared signal and appropriate circuitry can place the data on bus 1102. Bus 1102 carries the data to main memory 1106, from which processor 1104 retrieves and executes the instructions. The instructions received by main memory 1106 may optionally be stored on storage device 1110 either before or after execution by processor 1104.

Computer system 1100 also includes a communication interface 1118 coupled to bus 1102. Communication interface 1118 provides a two-way data communication coupling to a network link 1120 that is connected to a local network 1122. For example, communication interface 1118 may be an integrated services digital network ("ISDN") card or a modem to provide a data communication connection to a corresponding type of telephone line. As another example, communication interface 1118 may be a local area network ("LAN") card to provide a data communication connection to a compatible LAN. Wireless links may also be implemented. In any such implementation, communication interface 1118 sends and receives electrical, electromagnetic or optical signals that carry digital data streams representing various types of information.

Network link 1120 typically provides data communication through one or more networks to other data devices. For example, network link 1120 may provide a connection through local network 1122 to a host computer 1124 or to data equipment operated by an Internet Service Provider ("ISP") 1126. ISP 1126 in turn provides data communication services through the worldwide packet data communication network now commonly referred to as the "Internet" 1128. Local network 1122 and Internet 1128 both use electrical, electromagnetic or optical signals that carry digital data streams. The signals through the various networks and the signals on network link 1120 and through communication interface 1118, which carry the digital data to and from computer system 1100, are exemplary forms of carrier waves transporting the information.

Computer system 1100 can send messages and receive data, including program code, through the network(s), network link 1120 and communication interface 1118. In the Internet example, a server 1130 might transmit a requested code for an application program through Internet 1128, ISP 1126, local network 1122 and communication interface 1118. In accordance with the invention, one such downloaded application provides for digitally signing shared dynamic content as described herein.

The received code may be executed by processor 1104 as it is received, and/or stored in storage device 1110, or other non-volatile storage for later execution. In this manner, computer system 1100 may obtain application code in the form of a carrier wave.

5.0 Extensions and Alternatives

In the foregoing specification, the invention has been described with reference to specific embodiments thereof. It will, however, be evident that various modifications and changes may be made thereto without departing from the broader spirit and scope of the invention. For example, embodiments are applicable to treatment of vascular disease, hypertension, elevated cholesterol, and diabetes, and are useful in achieving stress reduction, addressing weight problems, smoking cessation, and improving personal lifestyle choices and habits. The specification and drawings are, accordingly, to be regarded in an illustrative rather than a restrictive sense.

What is claimed is:

1. A method of treating vascular disease in humans, the method comprising the computer-implemented steps of:
   (a) receiving, at a data center server that is communicatively coupled to a public data network, a first set of clinical vascular health data from a healthcare provider and representing a vascular health condition of a patient;
   (b) applying one or more vascular disease analysis algorithms to the first set of vascular health data, to result in creating and storing an initial treatment plan for the patient;
   (c) receiving a second set of vascular health data from a monitoring device that is associated with the patient and that is communicatively coupled to the data network, wherein the second set of vascular health data includes data from a Doppler vascular monitor;
   (d) applying one or more vascular analysis algorithms to result in creating one or more supplementary treatment plans for the patient, wherein at least one of the treatment plans includes a biofeedback interaction component;
   (e) providing the treatment plans to the patient over the data network;
   (f) iteratively repeating steps (c), (d) and (e) one or more times as determined by the patient, wherein one or more iterations include receiving patient data created after and resulting from the patient performing a biofeedback interaction and modifying the treatment plan based upon the resulting patient data, wherein the biofeedback interaction comprises the patient performing an action identified in the treatment plan while simultaneously (g) self-monitoring using the monitoring device and (h) observing output from the monitoring device, and the monitoring device generating the patient data during the performing of the action.

2. A method as recited in claim 1, wherein the initial treatment plan includes a biofeedback interaction component.

3. A method as recited in claim 1, wherein the monitoring device includes a Doppler vascular monitor that monitors vascular functions of the patient by attachment to locations proximate to a peripheral vascular system of the patient.

4. A method as recited in claim 1, further comprising the step of receiving data representing a selection, by the healthcare provider, of one or more parameter values that modify operation of one or more of the vascular disease analysis algorithms.

5. A method as recited in claim 1, wherein the initial treatment plan or the subsequent treatment plans comprise performing a biofeedback interaction using a client system of the patient.

6. A method as recited in claim 1, wherein step (c) further comprises displaying a multimedia vascular disease educational program to the patient.

7. A method as recited in claim 1, wherein step (c) further comprises the steps of generating and displaying, on the patient client system, a graphical representation of a vascular system anatomical element that is animated based on real-time data that is received from the patient using the monitoring device.

8. A method as recited in claim 1, wherein step (c) further comprises the steps of generating and displaying, on the patient client system, a graphical representation of vascular wall movement that is animated based on real-time data that is received from the patient using the monitoring device.

9. A method as recited in claim 1, wherein step (c) further comprises the steps of generating and graphically displaying, on the patient client system, one or more waveforms representing real-time patient physiological data received from the monitoring device.

10. A method as recited in claim 1, wherein the monitoring device includes a Doppler vascular monitor that monitors vascular functions of the patient by attachment to locations proximate to a peripheral vascular system of the patient, and wherein step (c) comprises the steps of generating and performing sound corresponding to data received from the Doppler vascular monitor.

11. A method as recited in claim 1, wherein the monitoring device includes a pulse monitor and wherein step (c) further comprises the steps of generating and graphically displaying one or more pulse waveforms corresponding to real-time pulse data received from the monitoring device.

12. A method as recited in claim 1, wherein the monitoring device includes a blood pressure monitor and wherein step (c) further comprises the steps of generating and graphically displaying one or more blood pressure waveforms corresponding to real-time blood pressure data received from the monitoring device.

13. A method as recited in claim 1, wherein step (c) comprises the steps of receiving a weight value or body mass index value as part of the second set of vascular health data.

14. A method as recited in claim 1, further comprising the steps of:
   receiving one or more third sets of vascular health data from the monitoring device before, during or after an exercise regimen performed by the patient;
   applying one or more vascular analysis algorithms to the third sets of vascular health data to result in generating a further supplemental treatment plan for the patient.

15. A method as recited in claim 14, further comprising the steps of generating and graphically displaying, on the patient client system, one or more waveforms representing real-time patient physiological data received from the monitoring device before, during or after the exercise regimen performed by the patient.

16. A method as recited in claim 1, further comprising the steps of:
   receiving patient nutritional data representing one or more nutritional habits then currently followed by the patient; and
   applying one or more dietary analysis algorithms based on the nutritional data and the vascular health data, to result in generating a nutritional plan for the patient.

17. A method as recited in claim 1, further comprising the steps of:
   receiving, from a video camera associated with the patient that is communicatively coupled to the data network, one or more sets of video data representing images of the patient performing one or more of the treatment plans;
   providing the one or more sets of video data to the healthcare provider over the public data network; and
   receiving, from the healthcare provider, one or more modifications to the treatment plans based on analysis of the video data by the healthcare provider.

18. A method as recited in claim 1, further comprising the steps of:
   receiving, from a digital still frame camera associated with the patient that is communicatively coupled to the data network, one or more digital images of the patient performing one or more of the treatment plans;

providing the one or more digital images to the healthcare provider over the public data network; and receiving, from the healthcare provider, one or more modifications to the treatment plans based on analysis of the digital images by the healthcare provider.

19. A method as recited in claim 1, further comprising the steps of:

determining, based on the vascular health data or the second set of vascular health data, one or more risk values associated with the patient and one or more advisory recommendations based on the risk values; and communicating the risk values and advisory recommendations to the healthcare provider and the patient over the public data network.

20. A method as recited in claim 19, further comprising the steps of:

determining whether the risk value is greater than a specified threshold associated with high risk;

when the risk value is greater than the specified threshold, then generating and communicating, to the healthcare provider and the patient over the public data network, a recommendation for the patient to consult with a healthcare provider in lieu of performing the treatment plans.

21. A method as recited in claim 1, further comprising the steps of:

receiving one or more third sets of vascular health data from the monitoring device before, during or after an administration of cardiovascular medication to the patient;

applying one or more vascular analysis algorithms to the third sets of vascular health data to result in generating a further supplemental treatment plan for the patient.

22. A method of generating digital data representing one or more plans for treating vascular disease in humans, the method comprising the computer-implemented steps of:

(a) receiving, at a data center server that is communicatively coupled to a public data network, a first set of clinical vascular health data from a healthcare provider and representing a vascular health condition of a patient;

(b) applying one or more vascular disease analysis algorithms to the first set of vascular health data, to result in creating and storing an initial treatment plan for the patient;

(c) receiving a second set of vascular health data from a monitoring device that is associated with the patient and that is communicatively coupled to the data network, wherein the second set of vascular health data includes data from a Doppler vascular monitor;

(d) applying one or more vascular analysis algorithms to result in creating one or more supplementary treatment plans for the patient, wherein at least one of the treatment plans includes a biofeedback interaction component;

(e) providing the treatment plans to the patient over the data network;

(f) iteratively repeating steps (c), (d) and (e) one or more times as determined by the patient, wherein one or more iterations of include receiving patient data created after and resulting from the patient performing a biofeedback interaction and modifying the treatment plan based upon the resulting patient data, wherein the biofeedback interaction comprises the patient performing an action identified in the treatment plan while simultaneously (g) self-monitoring using the monitoring device and (h) observing output from the monitoring device, and the monitoring device generating the patient data during the performing of the action.

* * * * *